United States Patent
Zhang et al.

(10) Patent No.: US 11,932,652 B2
(45) Date of Patent: *Mar. 19, 2024

(54) PYRROLIDINYL UREA DERIVATIVES AND APPLICATION THEREOF IN TrkA-RELATED DISEASES

(71) Applicant: ZHANGZHOU PIEN TZE HUANG PHARMACEUTICAL CO., LTD., Fujian (CN)

(72) Inventors: Yang Zhang, Shanghai (CN); Wentao Wu, Shanghai (CN); Zhixiang Li, Shanghai (CN); Jian Qin, Shanghai (CN); Jie Li, Shanghai (CN); Zhen Gong, Shanghai (CN); Jian Li, Shanghai (CN); Shuhui Chen, Shanghai (CN)

(73) Assignee: ZHANGZHOU PIEN TZE HUANG PHARMACEUTICAL CO., LTD., Fujian (CN)

( * ) Notice: Subject to any disclaimer, the term of this patent is extended or adjusted under 35 U.S.C. 154(b) by 601 days.

This patent is subject to a terminal disclaimer.

(21) Appl. No.: 17/259,811

(22) PCT Filed: Jul. 11, 2019

(86) PCT No.: PCT/CN2019/095576
§ 371 (c)(1),
(2) Date: Jan. 12, 2021

(87) PCT Pub. No.: WO2020/011227
PCT Pub. Date: Jan. 16, 2020

(65) Prior Publication Data
US 2021/0147436 A1 May 20, 2021

(30) Foreign Application Priority Data
Jul. 12, 2018 (CN) .................. 201810761702.X
Nov. 5, 2018 (CN) .................. 201811307582.2

(51) Int. Cl.
| C07D 491/048 | (2006.01) |
| C07D 403/14 | (2006.01) |
| C07D 471/04 | (2006.01) |
| C07D 487/04 | (2006.01) |

(52) U.S. Cl.
CPC ....... *C07D 491/048* (2013.01); *C07D 403/14* (2013.01); *C07D 471/04* (2013.01); *C07D 487/04* (2013.01)

(58) Field of Classification Search
CPC . C07D 491/048; C07D 403/14; C07D 471/04
See application file for complete search history.

(56) References Cited

U.S. PATENT DOCUMENTS

| 9,562,055 B2 | 2/2017 | Allen et al. |
| 10,160,727 B2 | 12/2018 | Nakamura et al. |
| 10,336,723 B2 | 7/2019 | Nagaswamy et al. |
| 10,533,006 B2 | 1/2020 | Yukimasa et al. |
| 10,640,495 B2 | 5/2020 | Yukimasa et al. |
| 2017/0240512 A1 | 8/2017 | Yukimasa et al. |

FOREIGN PATENT DOCUMENTS

| CN | 103649076 A | 3/2014 |
| CN | 107531589 A | 1/2018 |
| WO | 2012158413 A2 | 11/2012 |
| WO | 2014078323 A1 | 5/2014 |
| WO | 2016021629 A1 | 2/2016 |
| WO | 2016116900 A1 | 7/2016 |
| WO | 2017006953 A1 | 1/2017 |
| WO | 2017135399 A1 | 8/2017 |

OTHER PUBLICATIONS

European Search Report dated Mar. 30, 2022 issued in EP Application No. 19834894.8, 7 pages.
International Search Report dated Oct. 9, 2019 issued in International Application No. PCT/CN/2019/095576, with English translation, 8 pages.
Written Opinion of International Searching Authority dated Oct. 9, 2019 issued in International Application No. PCT/CN2019/095576, with English translation, 8 pages.
Notice of Reasons for Refusal dated Dec. 21, 2021 issued in JP Application No. 2021-500798, with English translation, 3 pages.
First Office Action dated Dec. 23, 2022 issued in CN Application No. 201980046866.7, with English translation, 14 pages.

*Primary Examiner* — Kamal A Saeed
(74) *Attorney, Agent, or Firm* — FOLEY & LARDNER LLP

(57) ABSTRACT

The present invention relates to a class of TrkA inhibitors and an application thereof in the preparation of a drug for the treatment of diseases associated with TrkA. The present invention specifically discloses compounds represented by formula (I) and formula (II), tautomer thereof or pharmaceutically acceptable salts thereof.

20 Claims, No Drawings

PYRROLIDINYL UREA DERIVATIVES AND APPLICATION THEREOF IN TrkA-RELATED DISEASES

CROSS-REFERENCE TO RELATED APPLICATIONS

The present application is a 371 of PCT/CN2019/095576, filed Jul. 11, 2019, which is based upon and claims priority to Chinese patent application 201810761702.X, filed on Jul. 12, 2018 and Chinese patent application 201811307582.2, filed on Nov. 5, 2018, which are hereby incorporated by reference in their entireties.

TECHNICAL FIELD

The present disclosure relates to a type of TrkA inhibitor, and a use thereof in the manufacture of a medicament for treating diseases related to TrkA. Specifically disclosed is compounds represented by formula (I) and formula (II) and pharmaceutically acceptable salts thereof. More specifically, the compounds of the present disclosure show TrkA kinase inhibitory effects and are suitable for the treatment of pain, cancer, inflammation, neurodegenerative diseases and certain infectious diseases.

BACKGROUND

Tropomyosin-related kinase (Trk) is a high affinity receptor tyrosine kinase activated by a group of soluble growth factors called nerve growth factor (NGF), brain-derived neurotrophic factor (BDNF), and neurotrophin (NT), and its family consists of three members (TrkA, TrkB, TrkC). NGF, BDNF, and NT-4/5 play an important role through the receptor Trk in neuronal cell signal maintenance, neuronal cell signal transmission, cell proliferation, cell differentiation, cell survival and many other physiological regulation processes. There is a lot of evidence that NGF/Trk signaling pathway inhibitors are effective in many preclinical models of pain; it has also been shown that NGF/Trk signaling pathway inhibitors are effective in many preclinical models of inflammatory diseases. In addition, the overexpression, activation, amplification and/or mutation of Trk kinase is associated with many tumors or cancers. Therefore, Trk has become an important therapeutic target, attracting extensive research and development interest. The TrkA inhibitors of the present disclosure can satisfy the treatment needs of pain, cancer, inflammation, neurodegenerative diseases and certain infectious diseases.

WO2015175788 reports a single compound with inhibitory activity on TrkA and the pharmaceutically acceptable salt thereof (see embodiment 8: reference compound D1). WO2012158413, WO2016116900, WO2016021629, and WO2017006953 report a series of compounds with inhibitory activity on TrkA, containing the pyrrolidinyl urea structure used in the present disclosure.

CONTENT OF THE PRESENT INVENTION

The present disclosure provides a compound represented by formula (I) and formula (II), an isomer thereof or a pharmaceutically acceptable salt thereof,

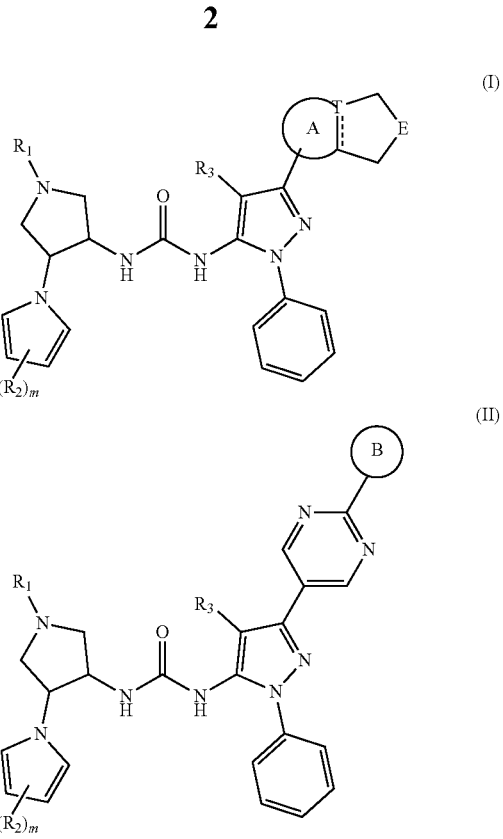

wherein,

⫽ is selected from a single bond and a double bond;
T is selected from N and C;
E is selected from O, $NR_4$ and $CR_5R_6$;
$R_1$ is selected from $C_{1-6}$ alkyl optionally substituted by 1, 2 or 3 $R_a$;
each of $R_2$ is independently selected from H, F, Cl, Br, I, OH and $NH_2$;
$R_3$ is selected from $C_{1-3}$ alkyl optionally substituted by 1, 2 or 3 $R_b$;
$R_4$ is selected from H, and $C_{1-6}$ alkyl optionally substituted by 1, 2 or 3 $R_c$;
each of $R_5$ and $R_6$ is independently selected from H, F, Cl, Br, I, OH, $NH_2$, CN, COOH, and $C_{1-3}$ alkyl optionally substituted by 1, 2 or 3 $R_d$;
ring A is selected from 5-6 membered heteroaryl;
ring B is selected from 4-6 membered heterocycloalkyl optionally substituted by 1, 2 or 3 $R_e$;
m is selected from 1, 2 and 3;
each of $R_a$, $R_b$, $R_c$, $R_d$ and $R_e$ is independently selected from F, Cl, Br, I, OH, $NH_2$, CN, COOH, $C_{1-3}$ alkyl and $C_{1-3}$ alkoxy, wherein the $C_{1-3}$ alkyl and $C_{1-3}$ alkoxy are optionally substituted by 1, 2 or 3 R;
R is selected from F, Cl, Br, I, OH and $NH_2$;
each of the 4-6 membered heterocycloalkyl and the 5-6 membered heteroaryl contains 1, 2, 3 or 4 heteroatoms or heteroatom groups independently selected from —NH—, —O—, —S— and N.

In some embodiments of the present disclosure, each of $R_a$, $R_b$, $R_c$, $R_d$ and $R_e$ is independently selected from F, Cl, Br, I, OH, $NH_2$, CN, COOH, $CH_3$ and $OCH_3$, and the other variables are as defined in the present disclosure.

In some embodiments of the present disclosure, $R_1$ is selected from $C_{1-3}$ alkyl optionally substituted by 1, 2 or 3 $R_a$, and the other variables are as defined in the present disclosure.

In some embodiments of the present disclosure, $R_1$ is selected from

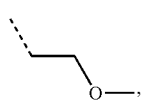

and the other variables are as defined in the present disclosure

In some embodiments of the present disclosure, $R_3$ is selected from $CH_3$ and $CH_2CH_3$, and the other variables are as defined in the present disclosure.

In some embodiments of the present disclosure, $R_4$ is selected from H and $C_{1-3}$ alkyl optionally substituted by 1, 2 or 3 $R_c$, and the other variables are as defined in the present disclosure.

In some embodiments of the present disclosure, $R_4$ is selected from H, $CH_3$, $CH_2CH_3$ and $CH_2CH_2OH$, and the other variables are as defined in the present disclosure.

In some embodiments of the present disclosure, each of $R_5$ and $R_6$ is independently selected from H, F, Cl, Br, I, OH, $NH_2$, CN, COOH and $CH_3$, and the other variables are as defined in the present disclosure.

In some embodiments of the present disclosure, ring A is selected from pyridyl and pyrazolyl, and the other variables are as defined in the present disclosure.

In some embodiments of the present disclosure, the structural unit

is selected from

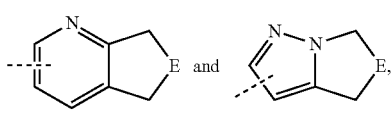

and the other variables are as defined in the present disclosure.

In some embodiments of the present disclosure, the structural unit

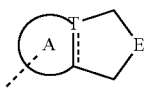

is selected from

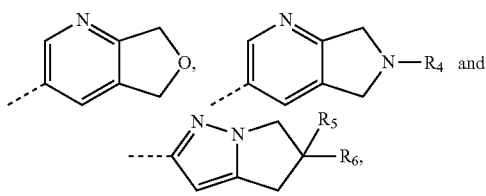

and the other variables are as defined in the present disclosure.

In some embodiments of the present disclosure, the structural unit

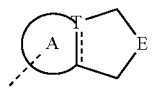

is selected from

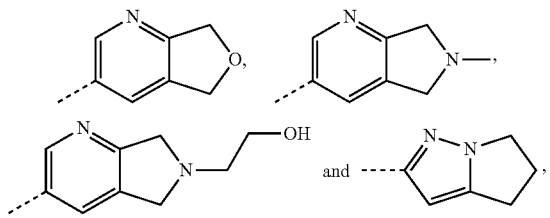

and the other variables are as defined in the present disclosure.

In some embodiments of the present disclosure, ring B is selected from oxetanyl and azetidinyl, wherein the oxetanyl and the azetidinyl are optionally substituted by 1, 2 or 3 $R_e$, and the other variables are as defined in the present disclosure.

In some embodiments of the present disclosure, ring B is selected from and

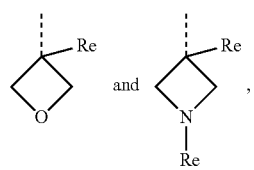

and the other variables are as defined in the present disclosure.

In some embodiments of the present disclosure, ring B is selected from

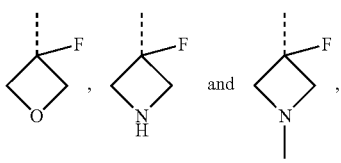

and the other variables are as defined in the present disclosure.

Some other embodiments of the present disclosure are obtained by arbitrary combination of the above variables.

In some embodiments of the present disclosure, the compound, the isomer or the pharmaceutically acceptable salt thereof is selected from

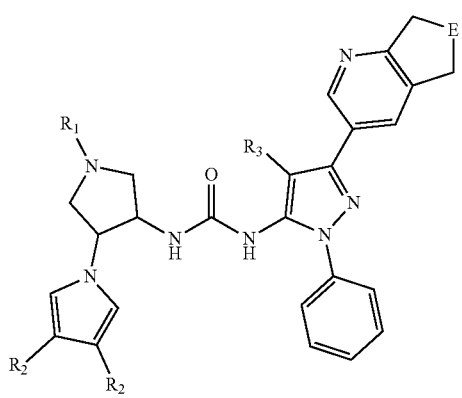
(I-1)
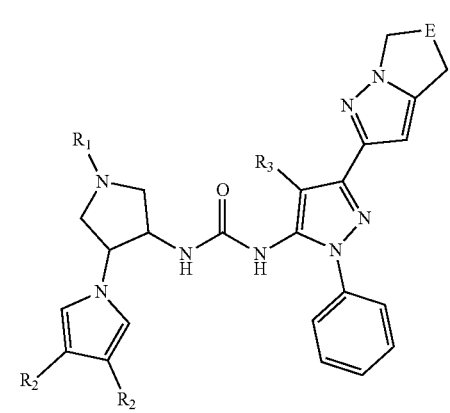
(I-2)
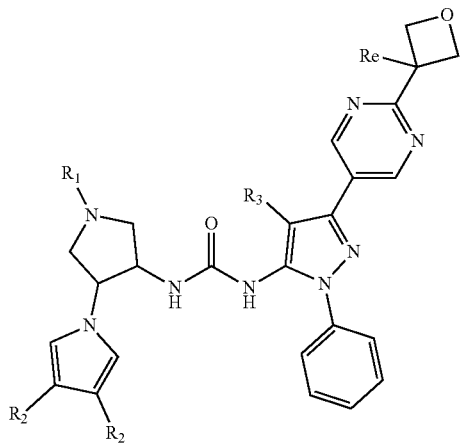
(I-3)
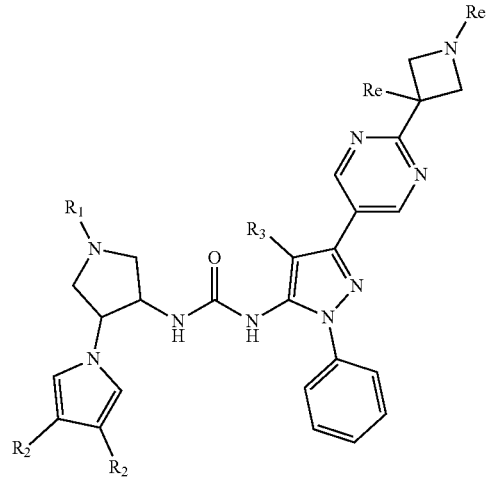
(I-4)
wherein,
E, $R_1$, $R_2$, $R_3$, $R_4$, $R_5$, $R_6$, and $R_c$ are as defined in the present disclosure.
In some embodiments of the present disclosure, the compound, the isomer or the pharmaceutically acceptable salt thereof is selected from
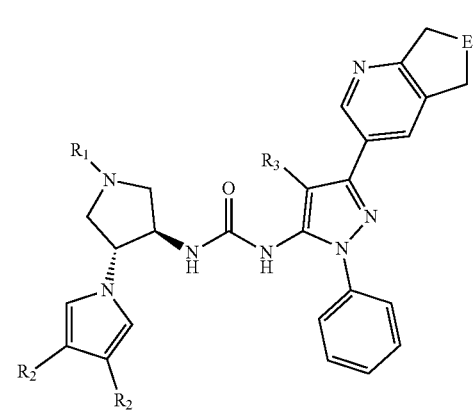
(I-1a)
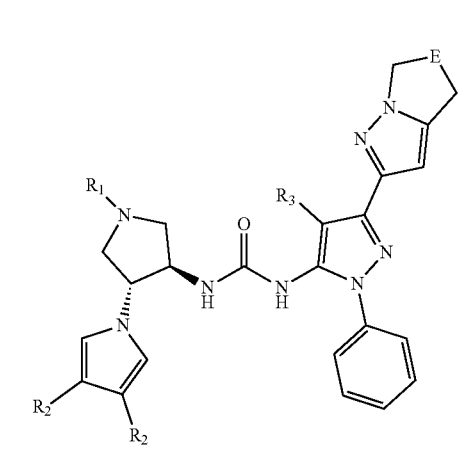
(I-2a)

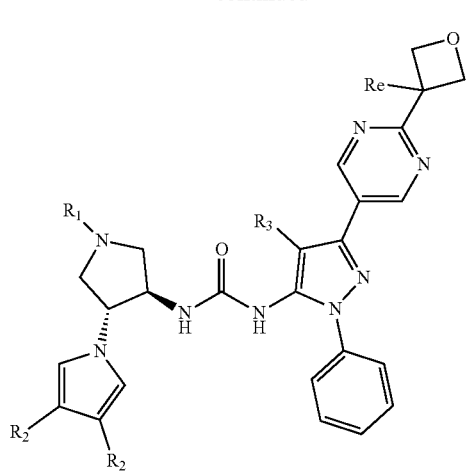
(I-3a)
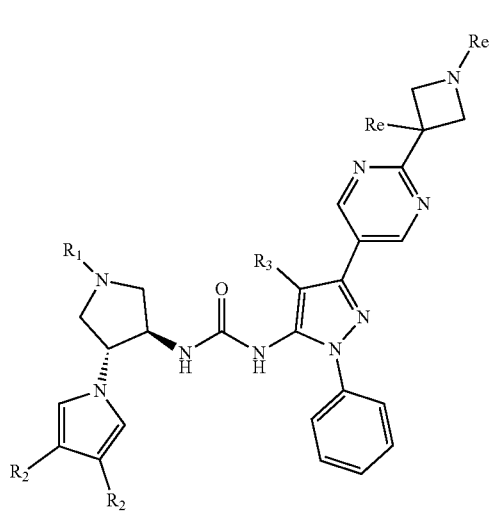
(I-4a)
wherein,
E, $R_1$, $R_2$, $R_3$, $R_4$, $R_5$, $R_6$, and $R_c$ are as defined in the present disclosure.
The present disclosure also provides a compound represented by the following formula, an isomer thereof or a pharmaceutically acceptable salt thereof, and the compound is selected from
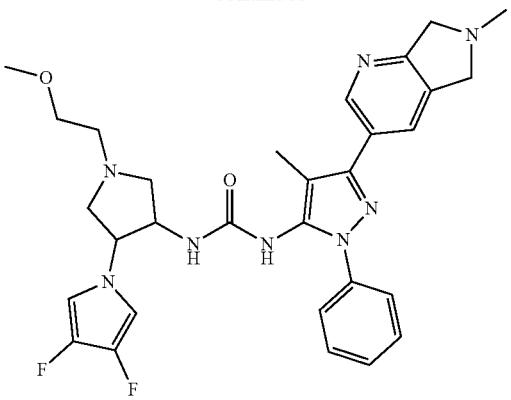
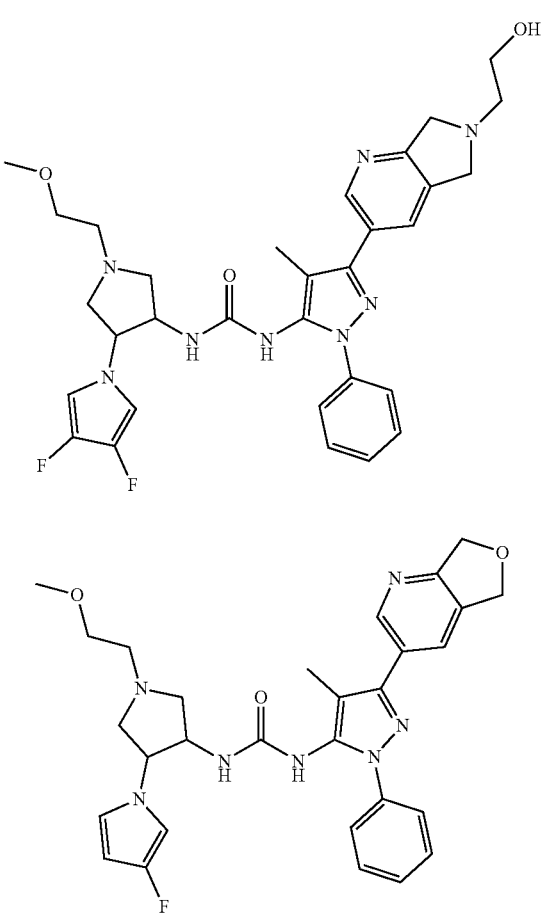
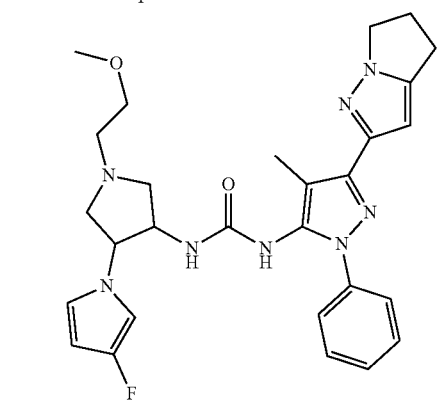

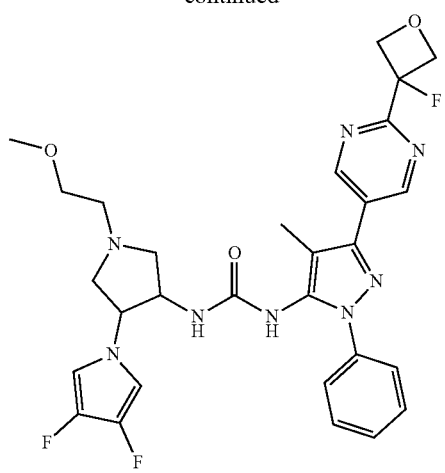
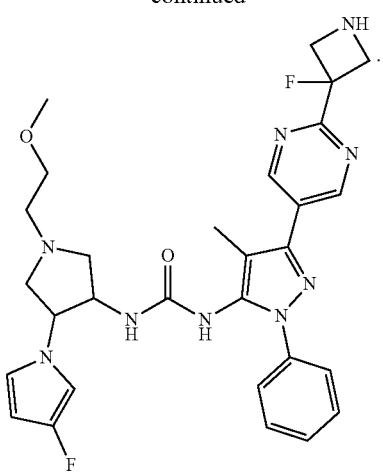
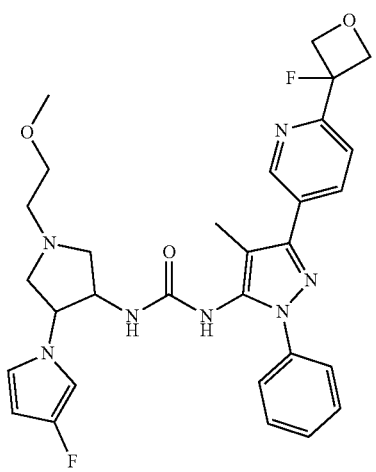
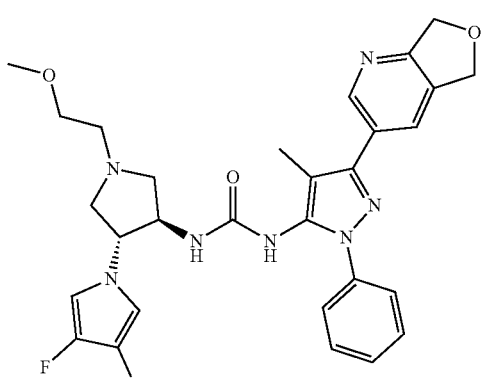
In some embodiments of the present disclosure, the compound is selected from
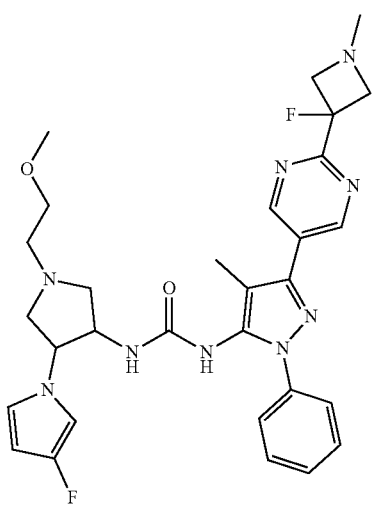
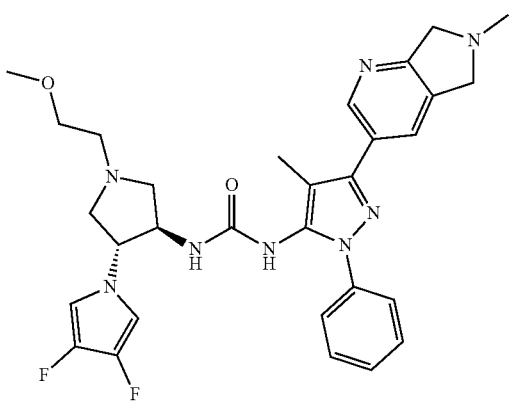

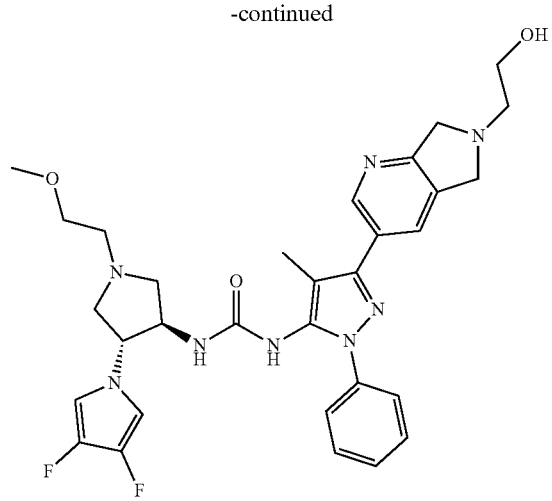
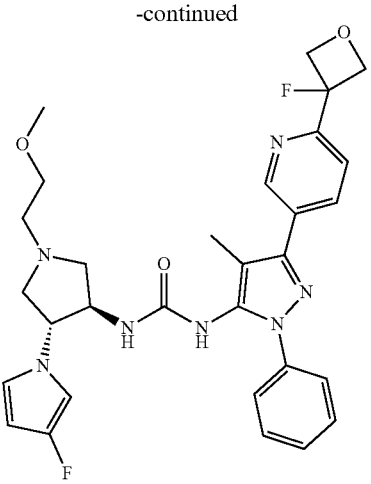

The present disclosure also provides a use of the compound, the isomer or the pharmaceutically acceptable salt thereof in the manufacture of a medicament for treating diseases related to TrkA inhibitors.

Definition and Description

Unless otherwise specified, the following terms and phrases when used herein have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium, or similar salts. When the compound of the present disclosure contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like. Certain specific compounds of the present disclosure contain both basic and acidic functional groups, thus can be converted to any base or acid addition salt.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

The compounds of the present disclosure may exist in specific geometric or stereoisomeric forms. The present disclosure contemplates all such compounds, including cis and trans isomers, (−)- and (+)-enantiomers, (R)- and (S)-enantiomers, diastereomers isomers, (D)-isomers, (L)-isomers, and racemic and other mixtures thereof, such as enantiomers or diastereomeric enriched mixtures, all of which are within the scope of the disclosure. Additional asymmetric carbon atoms may be present in substituents such as alkyl. All these isomers and their mixtures are included within the scope of the present disclosure.

Unless otherwise specified, the term "enantiomer" or "optical isomer" refers to stereoisomers that are mirror images of each other.

Unless otherwise specified, the term "cis-trans isomer" or "geometric isomer" is caused by the inability to rotate freely of double bonds or single bonds of ring-forming carbon atoms.

Unless otherwise specified, the term "diastereomer" refers to a stereoisomer in which a molecule has two or more chiral centers and the relationship between the molecules is not mirror images.

Unless otherwise specified, "(D)" or "(+)" refers to dextrorotation, "(L)" or "(−)" refers to levorotation, and "(DL)" or "(±)" refers to racemic.

Unless otherwise specified, the absolute configuration of a stereogenic center is represented by a wedged solid bond ( ) and a wedged dashed bond ( ), and the relative configuration of a stereogenic center is represented by a straight solid bond ( ) and a straight dashed bond ( ), a wave line ( ) is used to represent a wedged dashed bond ( ) or a wedged dashed bond ( ), or the wave line ( ) is used to represent a straight solid bond ( ) and a straight dashed bond ( ).

Unless otherwise specified, the term "tautomer" or "tautomeric form" means that at room temperature, the isomer of different functional groups are in dynamic equilibrium and can be transformed into each other quickly. If tautomers possibly exist (such as in solution), the chemical equilibrium of tautomers can be reached. For example, proton tautomer (also called prototropic tautomer) includes interconversion through proton migration, such as keto-enol isomerization and imine-enamine isomerization. Valence tautomer includes some recombination of bonding electrons for mutual transformation. A specific example of keto-enol tautomerization is the tautomerism between two tautomers of pentane-2,4-dione and 4-hydroxypent-3-en-2-one.

Unless otherwise specified, the terms "enriched in one isomer", "enriched in isomers", "enriched in one enantiomer" or "enriched in enantiomers" refer to the content of one of the isomer or enantiomers is less than 100%, and the content of the isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise specified, the term "isomer excess" or "enantiomeric excess" refers to the difference between the relative percentages of two isomers or two enantiomers. For example, if the content of one isomer or enantiomer is 90%, and the content of the other isomer or enantiomer is 10%, the isomer or enantiomer excess (ee value) is 80%.

Optically active (R)- and (S)-isomer, or D and L isomer can be prepared using chiral synthesis or chiral reagents or other conventional techniques. If one kind of enantiomer of certain compound of the present disclosure is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (such as carbamate generated from amine). The compound of the present disclosure may contain an unnatural proportion of atomic isotope at one or more than one atom(s) that constitute the compound. For example, the compound can be radiolabeled with a radioactive isotope, such as tritium ($^3H$), iodine-125 ($^{125}I$) or C-14 ($^{14}C$). For another example, deuterated drugs can be formed by replacing hydrogen with heavy hydrogen, the bond formed by deuterium and carbon is stronger than that of ordinary hydrogen and carbon, compared with non-deuterated drugs, deuterated drugs have the advantages of reduced toxic and side effects, increased drug stability, enhanced efficacy, extended biological half-life of drugs, etc. All isotopic variations of the compound of the present disclosure, whether radioactive or not, are encompassed within the scope of the present disclosure.

The term "optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted with the substituent, including deuterium and hydrogen variants, as long as the valence of the specific atom is normal and the substituted compound is stable. When the substituent is an oxygen (i.e., =O), it means two hydrogen atoms are substituted. Positions on an aromatic ring cannot be substituted with an oxo group. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of the variables is selected from a single bond, it means that the two groups linked by the single bond are connected directly. For example, when L in A-L-Z represents a single bond, the structure of A-L-Z is actually A-Z.

When a substituent is vacant, it means that the substituent does not exist. For example, when X is vacant in A-X, the structure of A-X is actually A. When the enumerative substituent does not indicate by which atom it is linked to the group to be substituted, such substituent can be bonded by any atom thereof. For example, when pyridyl acts as a substituent, it can be linked to the group to be substituted by any carbon atom on the pyridine ring. When the enumerative linking group does not indicate the direction for linking, the direction for linking is arbitrary, for example, the linking group L contained in

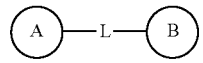

is -M-W—, then -M-W— can link ring A and ring B to form

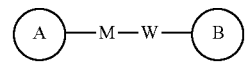

in the direction same as left-to-right reading order, and form

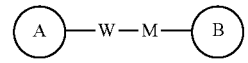

in the direction contrary to left-to-right reading order. A combination of the linking groups, substituents and/or variants thereof is allowed only when such combination can result in a stable compound.

Unless otherwise specified, the term "$C_{1-6}$ alkyl" refers to a linear or branched saturated hydrocarbon group containing 1 to 6 carbon atoms. The $C_{1-6}$ alkyl group includes $C_{1-5}$, $C_{1-4}$, $C_{1-3}$, $C_{1-2}$, $C_{2-6}$, $C_{2-4}$, $C_6$ and $C_5$ alkyl groups and the like; it can be monovalent (such as methyl), divalent (such as methylene) or multivalent (such as methine). Examples of $C_{1-6}$ alkyl include but are not limited to methyl (Me), ethyl (Et), propyl (including n-propyl and isopropyl), butyl (including n-butyl, isobutyl, s-butyl, and t-butyl), pentyl (including n-pentyl, isopentyl and neopentyl), hexyl, etc.

Unless otherwise specified, the term "$C_{1-3}$ alkyl" refers to a linear or branched saturated hydrocarbon group composed of 1 to 3 carbon atoms. The $C_{1-3}$ alkyl group includes $C_{1-2}$, and $C_{2-3}$ alkyl groups and the like; it can be monovalent (such as methyl), divalent (such as methylene) or multivalent (such as methine). Examples of $C_{1-4}$ alkyl include but are not limited to methyl (Me), ethyl (Et), propyl (including n-propyl and isopropyl), etc.

Unless otherwise specified, the term "$C_{1-3}$ alkoxy" refers to the alkyl groups containing 1 to 3 carbon atoms which is attached to the rest of the molecule through an oxygen atom. The $C_{1-3}$ alkoxy includes $C_{1-2}$, $C_{2-3}$, $C_3$ and $C_2$ alkoxy groups and the like. Examples of $C_{1-3}$ alkoxy include but are not limited to methoxy, ethoxy, propoxy (including n-propoxy and isopropoxy) and the like.

Unless otherwise specified, the term "4-6 membered heterocycloalkyl" by itself or in combination with other terms refers to saturated cyclic group consisting of 4 to 6 ring atoms, wherein 1, 2, 3 or 4 ring atoms are heteroatoms independently selected from O, S and N, and the rest are carbon atoms, the nitrogen atoms are optionally quaternized, and the nitrogen and sulfur heteroatoms are optionally oxidized (i.e., NO and S(O)$_p$, p is 1 or 2). It includes monocyclic and bicyclic ring systems, wherein bicyclic ring system includes spiro ring, fused ring, and bridged ring. In addition, with regard to the "4-6 membered heterocycloalkyl", a heteroatom may occupy the linking position of the heterocycloalkyl with the rest of the molecule. The 4-6 membered heterocycloalkyl includes 5-6 membered, 4 membered, 5 membered and 6 membered heterocycloalkyl groups. Examples of 4-6 membered heterocycloalkyl include, but are not limited to, azetidinyl, oxetanyl, thietanyl, pyrrolidinyl, pyrazolidinyl, imidazolidinyl, tetrahydrothienyl (including tetrahydrothiophen-2-yl and tetrahydrothiophen-3-yl, etc.), tetrahydrofuranyl (including tetrahydrofuran-2-yl, etc.), tetrahydropyranyl, piperidyl (including 1-piperidyl, 2-piperidyl and 3-piperidyl, etc.), piperazinyl (including 1-piperazinyl and 2-piperazinyl, etc.), morpholinyl (including 3-morpholinyl and 4-morpholinyl, etc.), dioxanyl, dithianyl, isoxazolidinyl, isothiazolidinyl, 1,2-oxazinyl, 1,2-thiazinyl, hexahydropyridazinyl, homopiperazinyl, or homopiperidyl, etc.

Unless otherwise specified, the terms "5-6 membered heteroaromatic ring" and "5-6 membered heteroaryl group" can be used interchangeably in the present disclosure, the term "5-6 membered heteroaryl group" refers to a ring composed of a monocyclic group with a conjugated 7-electron system consisting of 5 to 6 ring atoms, in which 1, 2, 3 or 4 ring atoms are heteroatoms independently selected from O, S and N, and the rest are carbon atoms. Wherein the nitrogen atom is optionally quaternized, the nitrogen and sulfur heteroatoms may optionally be oxidized (i.e., NO and $S(O)_p$, p is 1 or 2). The 5-6 membered heteroaryl group can be attached to the rest of the molecule through a heteroatom or a carbon atom. The 5-6 membered heteroaryl group includes 5-membered and 6-membered heteroaryl groups. Examples of the 5-6 membered heteroaryl include, but are not limited to, pyrrolyl (including N-pyrrolyl, 2-pyrrolyl and 3-pyrrolyl, etc.), pyrazolyl (including 2-pyrazolyl and 3-pyrrolyl), imidazolyl (including N-imidazolyl, 2-imidazolyl, 4-imidazolyl and 5-imidazolyl, etc.), oxazolyl (including 2-oxazolyl, 4-oxazolyl and 5-oxazolyl, etc.), triazolyl (1H-1,2,3-triazolyl, 2H-1,2,3-triazolyl, 1H-1,2,4-triazolyl and 4H-1,2,4-triazolyl, etc.), tetrazolyl, isoxazolyl (3-isoxazolyl, 4-isoxazolyl and 5-isoxazolyl, etc.), thiazolyl (including 2-thiazolyl, 4-thiazolyl and 5-thiazolyl, etc.), furyl (including 2-furyl and 3-furyl, etc.), thienyl (including 2-thienyl and 3-thienyl, etc.), pyridyl (including 2-pyridyl, 3-pyridyl, 4-pyridyl, etc.), pyrazinyl or pyrimidinyl (including 2-pyrimidinyl and 4-pyrimidinyl, etc.).

Unless otherwise specified, $C_{n-n+m}$ or $C_n-C_{n+m}$ includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$, and any range from n to n+m is also included, for example $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, and $C_{9-12}$, etc.; similarly, n-membered to n+m-membered means that the number of atoms in ring is from n to n+m, for example, 3-12 membered ring includes 3-membered ring, 4-membered ring, 5-membered ring, 6-membered ring, 7-membered ring, 8-membered ring, 9-membered ring, 10-membered ring, 11-membered ring, and 12-membered ring, and any range from n to n+m is also included, for example, 3-12 membered ring includes 3-6 membered ring, 3-9 membered ring, 5-6 membered ring, 5-7 membered ring, 6-7 membered ring, 6-8 membered ring, and 6-10 membered ring, etc.

The term "leaving group" refers to a functional group or atom which can be replaced by another functional group or atom through a substitution reaction (such as affinity substitution reaction). For example, representative leaving groups include triflate; chlorine, bromine, and iodine; sulfonate group, such as mesylate, tosylate, p-bromobenzenesulfonate, p-toluenesulfonates and the like; acyloxy, such as acetoxy, trifluoroacetoxy and the like.

The term "protecting group" includes, but is not limited to "amino protecting group", "hydroxy protecting group" or "thio protecting group". The term "amino protecting group" refers to a protecting group suitable for blocking the side reaction on the nitrogen of an amino. Representative amino protecting groups include, but are not limited to: formyl; acyl such as alkanoyl (e.g., acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-bis-(4'-methoxyphenyl) methyl; silyl such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl such as methyl, ethyl, and tert-butyl; acyl such as alkanoyl (e.g., acetyl); arylmethyl such as benzyl (Bn), p-methoxybenzyl (PMB), 9-fluorenylmethyl (Fm), and diphenylmethyl (benzhydryl, DPM); silyl such as trimethylsilyl (TMS) and tert-butyl dimethyl silyl (TBS) and the like.

The compounds of the present disclosure can be prepared by a variety of synthetic methods known to those skilled in the art, including the specific embodiments listed below, the embodiments formed by their combination with other chemical synthesis methods, and equivalent alternatives known to those skilled in the art, preferred implementations include but are not limited to the embodiments of the present disclosure.

The solvents used in the present disclosure are commercially available. The present disclosure uses the following abbreviations: aq represents water; HATU represents O-(7-azabenzotriazol-1-yl)-N,N,N',N'-tetramethylurea hexafluorophosphate; EDC represents N-(3-dimethylaminopropyl)-N'-ethylcarbodiimide hydrochloride; m-CPBA represents 3-chloroperoxybenzoic acid; eq represents equivalent; CDI represents carbonyl diimidazole; DCM represents dichloromethane; PE represents petroleum ether; DIAD represents diisopropyl azodicarboxylate; DMF represents N,N-dimethylformamide; DMSO represents dimethyl sulfoxide; EtOAc represents ethyl acetate; EtOH represents ethanol; MeOH represents methanol; CBz represents benzyloxycarbonyl, which is an amine protecting group; BOC represents tert-butoxycarbonyl, which is an amine protecting group; HOAc represents acetic acid; $NaCNBH_3$ represents sodium cyanoborohydride; rt represents room temperature; O/N represents overnight; THF represents tetrahydrofuran; $Boc_2O$ represents di-tert-butyl dicarbonate; TFA represents trifluoroacetic acid; DIPEA represents diisopropylethylamine; $SOCl_2$ represents thionyl chloride; $CS_2$ represents carbon disulfide; TsOH represents p-toluenesulfonic acid; NFSI represents N-fluoro-N-(benzenesulfonyl)benzenesulfonamide; NCS represents 1-chloropyrrolidine-2,5-dione; n-$Bu_4NF$ represents tetrabutylammonium fluoride; iPrOH represents 2-propanol; mp represents melting point; LDA represents lithium diisopropylamide; LiHMDS represents lithium hexamethyldisilazide; Xantphos represents 4,5-bis(diphenylphosphino)-9,9-dimethylxanthene; $LiAlH_4$ represents lithium aluminum hydride; $Pd(dba)_2$ represents tris (dibenzylideneacetone)dipalladium; mCPBA represents m-chloroperoxybenzoic acid; $Pd(dppf)Cl_2$ represents [1,1'-bis(diphenylphosphino)ferrocene]palladium dichloride.

The compounds of the present disclosure are named manually or using ChemDraw® software, and the commercially available compounds use the supplier catalog names.

Technical Effect

The compound of the present disclosure has a significant TrkA enzyme inhibitory effect; it has a higher human plasma protein free binding rate and a lower risk of drug-drug interaction; moreover, it has excellent metabolic stability of liver microsome in humans and rats.

DETAILED DESCRIPTION OF THE EMBODIMENT

The present disclosure will be described in detail below through examples, but they are not meant to impose any disadvantageous restriction to the present disclosure. The present disclosure has been described in detail herein, and its specific embodiments are also disclosed, it's obvious to those skilled in the art that various changes and improvements can be made to the specific embodiments of the present disclosure without departing from the spirit and scope of the present disclosure.

Reference Example 1: Synthesis of Intermediate L1

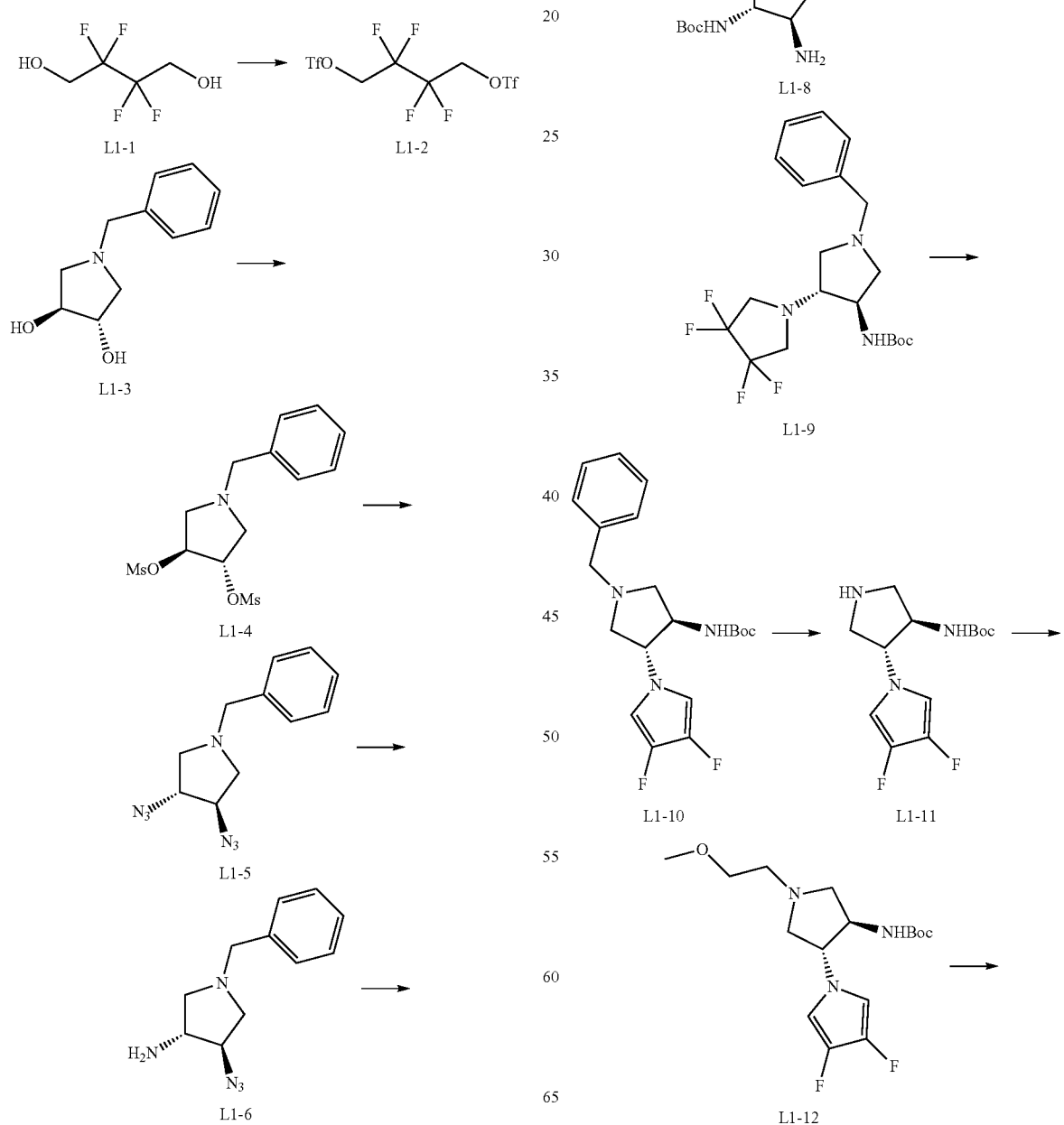

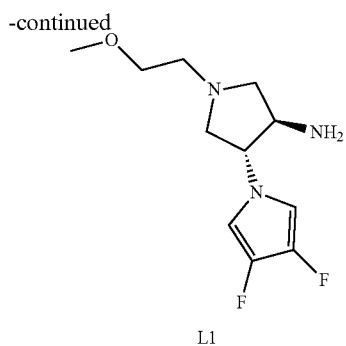

L1

Step 1: Preparation of Compound L1-2

Under an ice-water bath, compound L1-1 (9 g, 55.53 mmol) was dissolved in dichloromethane (100 mL), pyridine (10.98 g, 138.82 mmol) was then added thereto, a solution of trifluoromethanesulfonic anhydride (39.17 g, 138.82 mmol) in dichloromethane (20 mL) was slowly added dropwise, and the reaction mixture was slowly warmed to 25° C. and stirred for 18 hours. The reaction mixture was diluted with 500 mL of dichloromethane, washed successively with 500 mL of 1N hydrochloric acid and 500 mL of saturated brine, dried over anhydrous sodium sulfate, filtered, and the organic solvent was removed under reduced pressure to give compound L1-2. $^1$H NMR (400 MHz, CDCl$_3$) δ: 4.84-4.68 (m, 4H).

Step 2: Preparation of Compound L1-4

Under an ice-water bath, compound L1-3 (8.7 g, 45.02 mmol) was dissolved in dichloromethane (60 mL), triethylamine (13.67 g, 135.06 mmol) was added thereto, and methanesulfonyl chloride (11.35 g, 99.05 mmol) was slowly added dropwise, the reaction mixture was slowly warmed to 25° C. and stirred for 3 hours. 80 mL of water was added to the reaction mixture, extracted with dichloromethane (80 mL×2), and the combined organic phase was washed with 150 mL of saturated brine, dried over anhydrous sodium sulfate, filtered, and the organic solvent was removed under reduced pressure to give a crude product, which was purified by silica gel column chromatography (eluent: 20-50% EtOAc/PE) to give the compound L1-4. $^1$H NMR (400 MHz, CDCl$_3$) δ: 7.38-7.21 (m, 5H), 5.12 (t, J=4.8 Hz, 2H), 3.70-3.55 (m, 2H), 3.14-3.08 (m, 2H), 3.07 (s, 6H), 2.75 (dd, J=4.0, 10.8 Hz, 2H).

Step 3: Preparation of Compound L1-5

Compound L1-4 (15 g, 42.93 mmol) was dissolved in N,N-dimethylformamide (100 mL), then sodium azide (8.37 g, 128.78 mmol) was added thereto, the reaction mixture was heated to 100° C. and stirred for 16 hours. 200 mL of water was added to the reaction mixture after cooling, extracted with ethyl acetate (200 mL×3), and the combined organic phase was washed with water (300 mL×2) and saturated brine (300 mL) successively, dried over anhydrous sodium sulfate, filtered, and the organic solvent was removed under reduced pressure. The crude product obtained was purified by silica gel column chromatography (eluent: 0-2% EtOAc/PE) to give compound L1-5. $^1$H NMR (400 MHz, CDCl$_3$) δ: 7.43-7.28 (m, 5H), 3.90 (t, J=4.4 Hz, 2H), 3.75-3.61 (m, 2H), 3.02 (dd, J=6.4, 10.0 Hz, 2H), 2.70-2.58 (m, 2H).

Step 4: Preparation of Compound L1-6

Compound L1-5 (7 g, 28.77 mmol) was dissolved in tetrahydrofuran (60 mL), then water (1.04 g, 57.55 mmol) was added thereto, and triphenylphosphine (6.79 g, 25.90 mmol) was slowly added in batches; the reaction mixture was stirred at 25° C. until no more gas emission and then raised to 80° C. and stirred for 1 hour. After cooling, the organic solvent was removed under reduced pressure, 80 mL of 4N hydrochloric acid was added to the crude product obtained, extracted with 80 mL of dichloromethane, the pH value of the aqueous phase was adjusted to 10 with aqueous ammonia, extracted with dichloromethane (80 mL×2); the combined organic phase was washed with 100 mL of saturated brine, dried over anhydrous sodium sulfate, filtered, and the organic solvent was removed under reduced pressure to give the crude compound L1-6, which was directly used in the next reaction without further purification. $^1$H NMR (400 MHz, CDCl$_3$) δ: 7.35-7.24 (m, 5H), 3.64 (q, J=13.2 Hz, 2H), 3.56 (td, J=3.6, 6.8 Hz, 1H), 3.48-3.40 (m, 1H), 3.07-2.90 (m, 2H), 2.64 (dd, J=4.4, 10.4 Hz, 1H), 2.31 (dd, J=5.2, 9.6 Hz, 1H).

Step 5: Preparation of Compound L1-7

Compound L1-6 (6.4 g, 29.46 mmol) was dissolved in dichloromethane (60 mL), triethylamine (5.96 g, 58.91 mmol) and di-tert-butyl dicarbonate (7.71 g, 35.35 mmol) were added thereto, and the reaction solution was stirred at 25° C. for 15 hours. The organic solvent was removed under reduced pressure, and the crude product obtained was purified by silica gel column chromatography (eluent: 0-10% EtOAc/PE) to give compound L1-7. $^1$H NMR (400 MHz, CDCl$_3$) δ: 7.40-7.25 (m, 5H), 4.87 (s, 1H), 4.07 (s, 1H), 3.81 (s, 1H), 3.70-3.56 (m, 2H), 3.07 (dd, J=6.8, 10.4 Hz, 1H), 2.93-2.77 (m, 1H), 2.56-2.32 (m, 2H), 1.47 (s, 9H).

Step 6: Preparation of Compound L1-8

Compound L1-7 (8.8 g, 27.73 mmol) was dissolved in methanol (100 mL), palladium on carbon (0.5 g, 27.73 mmol, 10% purity) was added thereto, and the reaction mixture was stirred at 20° C. for 3 hours under 15 psi hydrogen. The reaction mixture was filtered through diatomite and the organic solvent was removed under reduced pressure to give the crude compound L1-8, which was directly used in the next reaction without further purification. $^1$H NMR (400 MHz, CDCl$_3$) δ: 7.33-7.25 (m, 5H), 5.04 (d, J=6.4 Hz, 1H), 3.70 (s, 1H), 3.63-3.54 (m, 2H), 3.34-3.23 (m, 1H), 3.07 (t, J=8.4 Hz, 1H), 2.82 (dd, J=7.2, 9.6 Hz, 1H), 2.51-2.43 (m, 1H), 2.21-2.09 (m, 1H), 1.44 (s, 9H).

Step 7: Preparation of Compound L1-9

Compound L1-8 (6 g, 20.59 mmol) was dissolved in ethanol (80 mL), compound L1-2 (8.78 g, 20.59 mmol) and triethylamine (10 mL) were added thereto, and the reaction mixture was heated to 90° C. and stirred for 16 hours. After cooling, the organic solvent was removed under reduced pressure, the crude product obtained was diluted with 300 mL of ethyl acetate, washed with 300 mL of saturated brine, dried over anhydrous sodium sulfate, filtered, and the organic solvent was removed under reduced pressure; the crude product obtained was purified by silica gel column chromatography (eluent: 0-20% EtOAc/PE) to give compound L1-9. $^1$H NMR (400 MHz, CDCl$_3$) δ: 7.39-7.29 (m, 5H), 4.98-4.86 (m, 1H), 4.05-4.01 (m, 1H), 3.64-3.53 (m, 2H), 3.24 (q, J=12.0 Hz, 2H), 3.12-2.90 (m, 3H), 2.80-2.59 (m, 3H), 2.23-2.14 (m, 1H), 1.46 (s, 9H).

Step 8: Preparation of Compound L1-10

Compound L1-9 (1 g, 2.40 mmol) was dissolved in dimethyl sulfoxide (10 mL), sodium tert-butoxide (690.66 mg, 7.19 mmol) was added thereto, and the reaction mixture was stirred at 100° C. for 16 hours. 30 mL of water was added to the reaction mixture after cooling, extracted with ethyl acetate (40 mL×3), and the combined organic phase was washed with 80 mL of saturated brine, dried over anhydrous sodium sulfate, filtered, and the organic solvent was removed under reduced pressure. The crude product obtained was purified by silica gel column chromatography (eluent: 0-15% EtOAc/PE) to give compound L1-10. $^1$H NMR (400 MHz, CDCl$_3$) δ: 7.31-7.20 (m, 5H), 6.41 (s, 2H), 4.69 (s, 1H), 4.09-3.89 (m, 2H), 3.64-3.50 (m, 2H), 3.05 (dd, J=7.2, 9.6 Hz, 1H), 2.96-2.85 (m, 1H), 2.71 (dd, J=4.0, 10.4 Hz, 1H), 2.29 (s, 1H), 1.36 (s, 9H). MS m/z: 378.1 [M+H]$^+$.

Step 9: Preparation of Compound L1-11

Compound L1-10 (0.35 g, 649.13 μmol) was dissolved in toluene (3 mL), diisopropylethylamine (117.45 mg, 908.78 μmol) was added thereto; under an ice-water bath, 1-chloroethyl a-chloroformate (120.65 mg, 843.87 μmol) was added dropwise; the reaction mixture was heated to 90° C. and stirred for 1 hour. After cooling, the reaction mixture was concentrated under reduced pressure, methanol (3 mL) was added to the crude product obtained, and stirred for 4 hours at 20° C. 20 mL of water was added to the reaction mixture, extracted with ethyl acetate (20 mL×2); the aqueous phase was concentrated to give crude compound L1-11, which was directly used in the next reaction without further purification. MS m/z: 288.3 [M+H]$^+$.

Step 10: Preparation of Compound L1-12

The crude product of compound L1-11 (0.30 g, 916.54 μmol) was dissolved in N,N-dimethylformamide (30.0 mL), diisopropylethylamine (947.63 mg, 7.33 mmol) and 2-bromoethyl methyl ether (636.95 mg, 4.58 mmol) were added, and the reaction mixture was stirred at 20° C. for 16 hours; diisopropylethylamine (473.83 mg, 3.67 mmol) and 2-bromoethyl methyl ether (254.78 mg, 1.83 mmol) were additionally added. The reaction mixture was stirred at 20° C. for 20 hours. 30 mL of water was added to the reaction mixture, extracted with ethyl acetate (50 mL×2), and the combined organic phase was washed with water (60 mL) and saturated brine (60 mL) successively, dried over anhydrous sodium sulfate, filtered, and the organic solvent was removed under reduced pressure to give compound L1-12, which was directly used in the next reaction without further purification. MS m/z: 346.3 [M+H]$^+$.

Step 11: Preparation of Compound L1

The crude product of compound L1-12 (130 mg, 376.39 μmol) was dissolved in dimethyl sulfoxide (12 mL), potassium tert-butoxide (211.18 mg, 1.88 mmol) was added, and the reaction mixture was heated to 100° C. under nitrogen atmosphere and stirred for 16 hours. 20 mL of water was added to the reaction mixture after cooling, extracted with ethyl acetate (30 mL×2), and the combined organic phase was washed with water (30 mL) and saturated brine (30 mL) successively, dried over anhydrous sodium sulfate, filtered, and the organic solvent was removed under reduced pressure to give compound L1, which was directly used in the next reaction without further purification. $^1$H NMR (400 MHz, CDCl$_3$) δ 6.45 (s, 2H), 3.90-3.83 (m, 1H), 3.54-3.43 (m, 3H), 3.38 (s, 3H), 3.20-3.12 (m, 1H), 3.08-3.02 (m, 1H), 2.75-2.95 (m, 1H), 2.79-2.71 (m, 1H), 2.69-2.61 (m, 1H), 2.37 (dd, J=6.8, 9.6 Hz, 1H). MS m/z: 246.2 [M+H]$^+$.

Reference Example 2: Synthesis of Intermediate L2

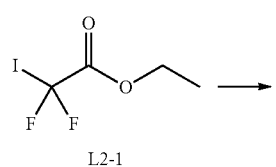

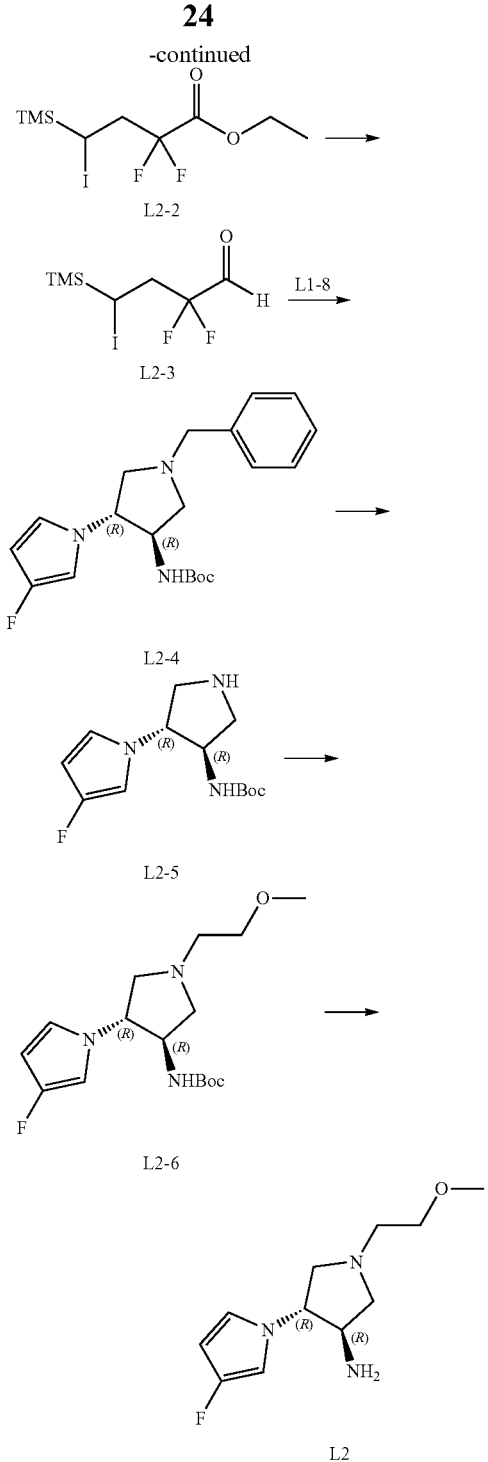

Step 1: Preparation of Compound L2-2

Compound L2-1 (15 g, 60.00 mmol) and vinyltrimethylsilane (12.03 g, 120.01 mmol) were dissolved in acetonitrile (150 mL), activated copper powder (190.65 mg, 3.00 mmol) was added, and the reaction mixture was heated to 65° C. and stirred for 15 hours. After cooling, the organic solvent was removed under reduced pressure, and the crude product obtained was purified by silica gel column chromatography (eluent: 0-5% EtOAc/PE) to give compound L2-2. $^1$H NMR (400 MHz, CDCl$_3$) δ: 4.18 (q, J=7.2 Hz, 2H), 2.94-2.90 (m, 1H), 2.52-2.37 (m, 2H), 1.20 (t, J=7.2 Hz, 3H), 0.00 (s, 9H).

Step 2: Preparation of compound L2-3

At −30° C., compound L2-2 (5 g, 14.28 mmol) was dissolved in anhydrous tetrahydrofuran (100 mL), diisobutylaluminum hydride (1 M, 28.55 mL) was slowly added dropwise, and the reaction mixture was slowly warmed to 20° C. and stirred for 2 hours. 60 mL of 0.5N hydrochloric acid was added to the reaction mixture, extracted with ethyl acetate (100 mL×2), and the combined organic phase was washed with 200 mL of saturated brine, dried over anhydrous sodium sulfate, filtered; the organic solvent was removed under reduced pressure to give crude compound L2-3, which was directly used in the next reaction without further purification.

Step 3: Preparation of Compound L2-4

Compound L1-8 (2.35 g, 8.06 mmol) was dissolved in acetonitrile (50 mL), compound L2-3 (1.98 g, 6.45 mmol) was added, and the reaction mixture was heated to 50° C. and stirred for 15 hours. After cooling, the organic solvent was removed under reduced pressure, and the crude product obtained was purified by silica gel column chromatography (eluent: 0-30% EtOAc/PE) to give compound L2-4. $^1$H NMR (400 MHz, CDCl$_3$) δ: 7.40-7.27 (m, 5H), 6.61 (s, 1H), 6.53 (s, 1H), 5.87 (dd, J=2.0, 2.8 Hz, 1H), 4.82 (s, 1H), 4.29-4.17 (m, 1H), 4.15-4.05 (m, 1H), 3.73-3.58 (m, 2H), 3.16-3.03 (m, 2H), 2.85-2.76 (m, 1H), 2.58-2.43 (m, 1H), 1.43 (s, 9H).

Step 4: Preparation of Compound L2-5

Compound L2-4 (840 mg, 2.34 mmol) was dissolved in toluene (30 mL), diisopropylethylamine (422.86 mg, 3.27 mmol) was added; under an ice-water bath, 1-chloroethyl a-chloroformate (434.35 mg, 3.04 mmol) was slowly added dropwise; the reaction mixture was heated to 90° C. and stirred for 1 hour. After cooling, the organic solvent was removed under reduced pressure, methanol (30 mL) was added, and the mixture was stirred at 20° C. for 17 hours. The organic solvent was removed under reduced pressure to give crude compound L2-5, which was directly used in the next reaction without further purification. MS m/z=270.1 [M+1]$^+$.

Step 5: Preparation of Compound L2-6

Compound L2-5 (630 mg, 2.34 mmol) was dissolved in N,N-dimethylformamide (10 mL), and diisopropylethylamine (906.98 mg, 7.02 mmol) and 2-bromoethyl methyl ether (536.92 mg, 3.51 mmol) were added; the reaction mixture was stirred at 20° C. for 64 hours. The reaction mixture was diluted by adding 100 mL of ethyl acetate, washed with 60 mL of water and 60 mL of saturated brine successively, dried over anhydrous sodium sulfate, filtered, and the organic solvent was removed under reduced pressure to give a crude product. The crude product obtained was purified by silica gel column chromatography (eluent: 25%-60% EtOAc/PE) to give compound L2-6. $^1$H NMR (400 MHz, CDCl$_3$) δ: 6.60 (s, 1H), 6.54 (s, 1H), 5.88 (dd, J=2.0, 2.8 Hz, 1H), 4.91 (s, 1H), 4.24 (s, 1H), 4.12-4.05 (m, 1H), 3.51 (t, J=5.6 Hz, 2H), 3.37 (s, 3H), 3.19 (s, 1H), 3.08 (d, J=8.0 Hz, 1H), 2.84-2.64 (m, 3H), 1.43 (s, 9H).

Step 6: Preparation of Compound L2

Compound L2-6 (100 mg, 305.44 μmol) was dissolved in dichloromethane (2 mL), trifluoroacetic acid (2 mL) was added, and the reaction mixture was stirred at 20° C. for 0.5 hour. The organic solvent was removed under reduced pressure to give crude compound L2, which was directly used in the next reaction without further purification. MS m/z=228.1 [M+1]$^+$.

Reference Example 3: Synthesis of Intermediate R1

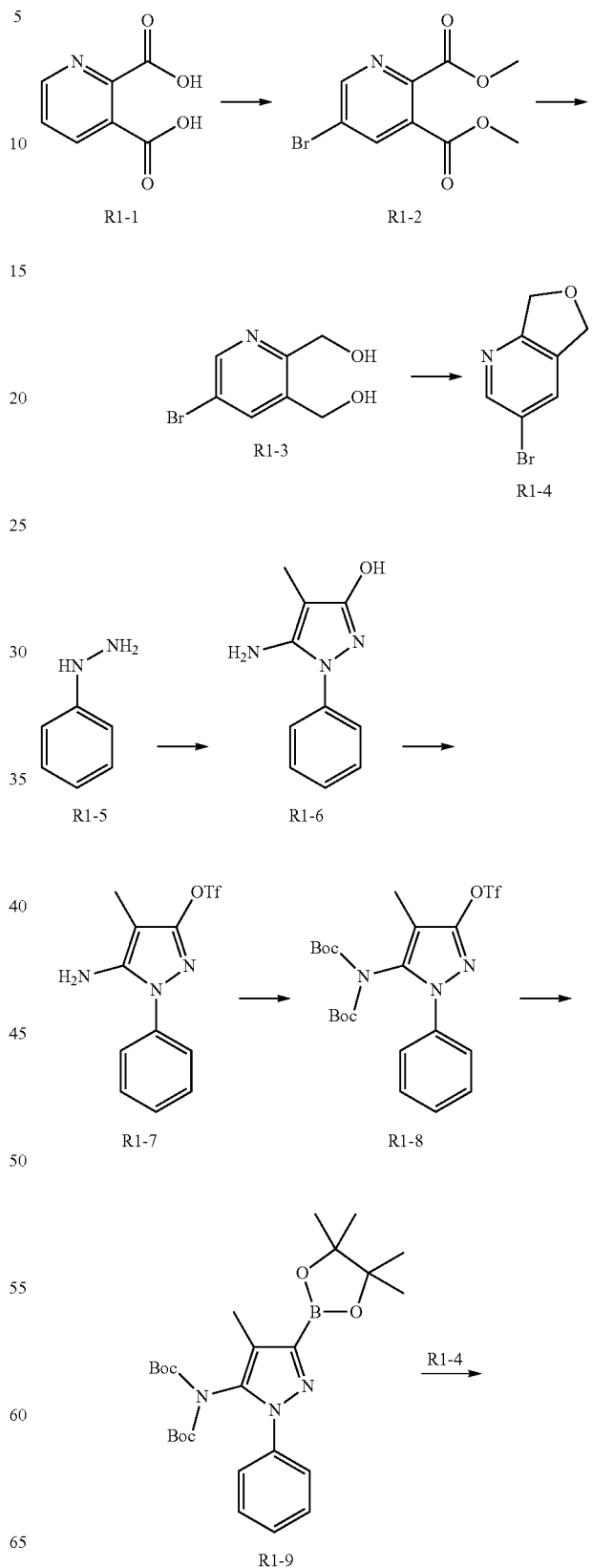

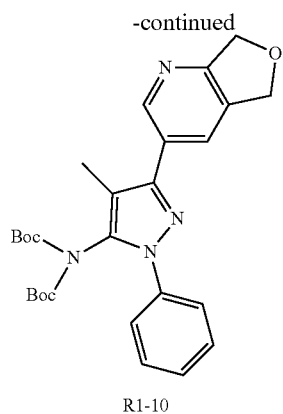

R1-10

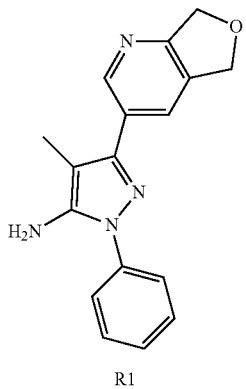

R1

Step 1: Preparation of Compound R1-2

Compound R1-1 (20.00 g, 119.68 mmol) was dissolved in methanol (200 mL), concentrated sulfuric acid (7.36 g, 75.04 mmol) was added dropwise, and the reaction mixture was heated to 70° C. and stirred for 29 hours. After cooling to 40° C., liquid bromine (47.81 g, 299.19 mmol) was added dropwise, and the reaction mixture was heated to 55° C. and stirred for 48 hours. 100 mL of sodium thiosulfate solution was added to the reaction mixture, which was then concentrated until a half volume of the mixture remained. The resulting crude product was extracted with ethyl acetate (200 mL×4), and the combined organic phase was washed with saturated brine (50 mL), dried over anhydrous sodium sulfate, filtered, and the organic solvent was removed under reduced pressure. The crude product obtained was purified by silica gel column chromatography (eluent: 0%-20% EtOAc/PE) to give compound R1-2. $^1$H NMR (400 MHz, CDCl$_3$) δ: 8.82 (d, J=2.28 Hz, 1H), 8.30 (d, J=2.28 Hz, 1H), 4.00 (s, 3H), 3.96 (s, 3H). MS m/z=273.8 [M+H]$^+$.

Step 2: Preparation of Compound R1-3

Under nitrogen atmosphere, R1-2 (12.00 g, 43.78 mmol) was dissolved in ethanol (150 mL), sodium borohydride (8.28 g, 218.92 mmol) was added, and the reaction mixture was stirred at 15° C. for 1.5 hours, then warmed to 80° C. and stirred for 15.5 hours. After hot filtration, the organic solvent was removed under reduced pressure, and the crude product obtained was purified by high performance liquid chromatography (column: Phenomenex luna C18 250*50 mm*10 m; mobile phase: [water (10 mM NH$_4$HCO$_3$)-ACN]; B %: 0%-30%, 25 min) to give compound R1-3. $^1$H NMR (400 MHz, CD$_3$OD) δ: 8.51-8.48 (m, 1H), 8.08-8.06 (m, 1H), 4.74 (s, 2H), 4.69 (s, 2H).

Step 3: Preparation of Compound R1-4

Under an ice water bath, R1-3 (0.80 g, 3.67 mmol) was dissolved in N,N-dimethylformamide (30.0 mL), sodium hydride (513 mg, 12.84 mmol, 60% purity) was added, and the mixture was stirred for 30 minutes; p-toluenesulfonyl chloride (259 mg, 3.67 mmol) was added, and the reaction mixture was warmed to 20° C. and stirred for 18 hours. 20 mL of water was added to the reaction mixture and partitioned, the aqueous phase was extracted with ethyl acetate (100 mL×2); the combined organic phase was washed with water (20 mL×2) and saturated sodium chloride solution (20 mL) successively, dried over anhydrous sodium sulfate, filtered, and the organic solvent was removed under reduced pressure. The crude product obtained was purified by silica gel column chromatography (eluent: 0%-20% EtOAc/PE) to give compound R1-4. $^1$H NMR (400 MHz, CDCl$_3$) δ: 8.55 (s, 1H), 7.70 (s, 1H), 5.16 (s, 2H), 5.03 (s, 2H).

Step 4: Preparation of Compound R1-6

R1-5 (20.00 g, 184.95 mmol) and ethyl 2-cyanopropionate (23.51 g, 184.95 mmol) were dissolved in 1,4-dioxane (40 mL), and the reaction mixture was heated to 110° C. and stirred for 72 hours. After cooling, the reaction mixture was concentrated to about 20 mL, during which a solid precipitated out. The mixture was filtered, and the filter cake was washed with ethyl acetate (30 mL) and then collected to give compound R1-6. $^1$H NMR (400 MHz, CD$_3$OD) δ: 7.53-7.46 (m, 2H), 7.42-7.35 (m, 3H), 1.77 (s, 3H).

Step 5: Preparation of Compound R1-7

Compound R1-6 (10.00 g, 52.85 mmol) was dissolved in N,N-dimethylformamide (150 mL), diisopropylethylamine (20.49 g, 158.55 mmol) and N-phenyl bis (trifluoromethanesulfonyl)imine (19.82 g, 55.49 mmol) were added successively, and the reaction mixture was stirred at 25° C. for 16 hours. The reaction mixture was poured into 500 mL of water, extracted with ethyl acetate (150 mL×3), and the combined organic phase was washed once with saturated brine (300 mL), dried over anhydrous sodium sulfate, filtered; the organic solvent was removed under reduced pressure to give crude compound R1-7, which was directly used in the next reaction without further purification. $^1$H NMR (400 MHz, CDCl$_3$) δ: 7.54-7.44 (m, 4H), 7.40-7.34 (m, 1H), 3.76 (s, 2H), 1.95 (s, 3H).

Step 6: Preparation of Compound R1-8

Compound R1-7 (1.00 g, 3.11 mmol) was dissolved in dichloromethane (5 mL), di-tert-butyl dicarbonate (2.04 g, 9.34 mmol), triethylamine (945 mg, 9.34 mmol) and 4-dimethylaminopyridine (38 mg, 311.26 μmol) were successively added, and the reaction mixture was stirred at 15° C. for 16.5 hours. The organic solvent was removed under reduced pressure, and the crude product obtained was purified by silica gel column chromatography (eluent: 0-11% EtOAc/PE) to give compound R1-8. $^1$H NMR (400 MHz, CDCl$_3$) δ: 7.37-7.26 (m, 5H), 1.89 (s, 3H), 1.20 (s, 18H). MS m/z: 522.0 [M+1]$^+$.

Step 7: Preparation of Compound R1-9

Compound R1-8 (1.00 g, 1.92 mmol) was dissolved in 1,4-dioxane (10 mL), bis(pinacolato)diboron (584 mg, 2.30 mmol), potassium acetate (565 mg, 5.57 mmol) and 1,1-bis (diphenylphosphino)ferrocene palladium dichloride dichloromethane complex (157 mg, 191.75 μmol) were successively added, and the reaction mixture was heated to 95° C. and stirred for 16 hours. The reaction mixture was filtered through diatomite, the organic solvent was removed under reduced pressure, and the crude product obtained was purified by silica gel column chromatography (eluent: 0-50% EtOAc/PE) to give compound R1-9. $^1$H NMR (400 MHz, CDCl$_3$) δ: 7.49-7.45 (m, 2H), 7.42-7.32 (m, 3H), 2.13 (s, 3H), 1.38 (s, 12H), 1.31 (s, 18H).

Step 8: Preparation of Compound R1-10

R1-4 (295 mg, 1.47 mmol) and compound R1-9 (1.10 g, 2.21 mmol) were dissolved in a mixed solution of 1,4-dioxane (3 mL) and water (0.3 mL), sodium carbonate (234 mg, 2.21 mmol) and [1,1'-bis(diphenylphosphino)ferrocene] palladium dichloride (108 mg, 147.48 μmol) were added, and the reaction mixture was heated to 100° C. and stirred for 15.5 hours. After cooling, the reaction mixture was filtered through diatomite, and the organic solvent was removed under reduced pressure to give crude compound R1-10, which was directly used in the next reaction without further purification.

Step 9: Preparation of Compound R1

Compound R1-10 (720 mg, 1.46 mmol) was dissolved in dichloromethane (5 mL), trifluoroacetic acid (5 mL) was added, and the reaction mixture was stirred at 20° C. for 1 hour. The reaction mixture was poured into saturated sodium bicarbonate solution (30 mL), extracted with dichloromethane (50 mL); the organic phase was washed with saturated brine (20 mL), dried over anhydrous sodium sulfate, filtered, and the organic solvent was removed under reduced pressure; the crude product obtained was purified by silica gel column chromatography (eluent: 11%-100% EtOAc/PE) to give compound R1. $^1$H NMR (400 MHz, CDCl$_3$) δ: 8.81 (s, 1H), 7.94 (s, 1H), 7.66-7.61 (m, 2H), 7.52 (t, J=8.0 Hz, 2H), 7.39 (t, J=8.0 Hz, 1H), 5.21 (s, 2H), 5.12 (s, 2H), 3.70 (s, 2H), 2.16 (s, 3H).

Reference Example 4: Synthesis of Intermediate R2

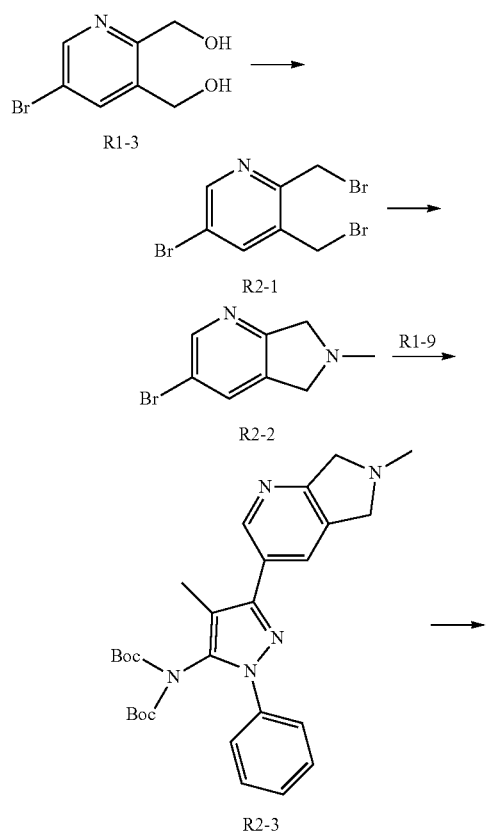

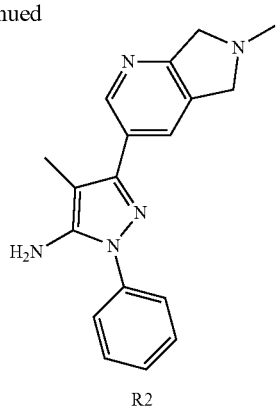

Step 1: Preparation of Compound R2-1

Compound R1-3 (1.4 g, 6.42 mmol) was dissolved in hydrogen bromide (55.13 g, 258.92 mmol, 38% purity), and the reaction mixture was heated to 130° C. and stirred for 24 hours; concentrated sulfuric acid (9.2 g, 91.92 mmol) was added and the reaction mixture was stirred for 24 hours. After cooling, saturated sodium bicarbonate solution was added to the reaction mixture to adjust pH to 7-8, extracted with dichloromethane (150 mL×3); the combined organic phase was dried over anhydrous sodium sulfate, filtered, and the organic solvent was removed under reduced pressure. The crude product obtained was purified by silica gel chromatography column (eluent: 0-10% EtOAc/PE) to give compound R$_2$-1. $^1$H NMR (400 MHz, CDCl$_3$) δ: 8.58 (d, J=2.0 Hz, 1H), 7.85 (d, J=2.0 Hz, 1H), 4.67 (s, 2H), 4.56 (s, 2H). MS m/z: 343.7 [M+H]*.

Step 2: Preparation of Compound R2-2

Under an ice-water bath, compound R2-1 (800 mg, 2.33 mmol) and methylamine hydrochloride (471.27 mg, 6.98 mmol) were dissolved in dichloromethane (5 mL), diisopropylethylamine (1.2 g, 9.31 mmol) was added, and the reaction mixture was stirred at this temperature for 1 hour, then slowly raised to 25° C. and stirred for 17 hours. The organic solvent was removed under reduced pressure, and the crude product obtained was purified by silica gel chromatography column (eluent: 10-100% EtOAc/PE) to give compound R2-2. $^1$H NMR (400 MHz, CDCl$_3$) δ: 8.46 (s, 1H), 7.64 (s, 1H), 3.98-3.91 (m, 4H), 2.62 (s, 3H).

Step 3: Preparation of Compound R2-3

Under nitrogen atmosphere, compound R2-2 (50.0 mg, 234.66 μmol) and compound R1-9 (105.47 mg, 211.19 μmol) were dissolved in a mixed solvent of dioxane (4 mL) and water (0.4 mL), followed by addition of [1,1'-bis(diphenylphosphino)ferrocene]palladium dichloride (17.17 mg, 23.47 μmol) and sodium carbonate (74.61 mg, 703.98 μmol); the reaction mixture was heated to 100° C. and stirred for 17 hours. After cooling, the organic solvent was removed under reduced pressure, and the crude product obtained was purified by silica gel chromatography column (eluent: 2-6% MeOH/DCM) to give compound R2-3. MS m/z: 506.2 [M+H]$^+$.

Step 4: Preparation of Compound R2

Compound R2-3 (120 mg, 237.34 μmol) was dissolved in dichloromethane (3 mL), trifluoroacetic acid (1 mL) was added, and the reaction mixture was stirred at 20° C. for 3 hours. Dichloromethane (15 mL) was added to the reaction mixture, and sodium bicarbonate solid (10.0 g) was added; the mixture was filtered, and the organic solvent was removed under reduced pressure to give crude compound R2, which was directly used in the next reaction without further purification. ¹H NMR (400 MHz, CDCl₃) δ: 8.90 (s, 1H), 8.03 (s, 1H), 7.64-7.59 (m, 2H), 7.56-7.50 (m, 2H), 7.43-7.38 (m, 1H), 4.52-4.48 (m, 1H), 3.98-3.93 (m, 1H), 3.84-3.79 (m, 1H), 3.78-3.68 (m, 2H), 3.66-3.61 (m, 1H), 3.07 (s, 3H), 2.16 (s, 3H).

Reference Example 5: Synthesis of Intermediate R3

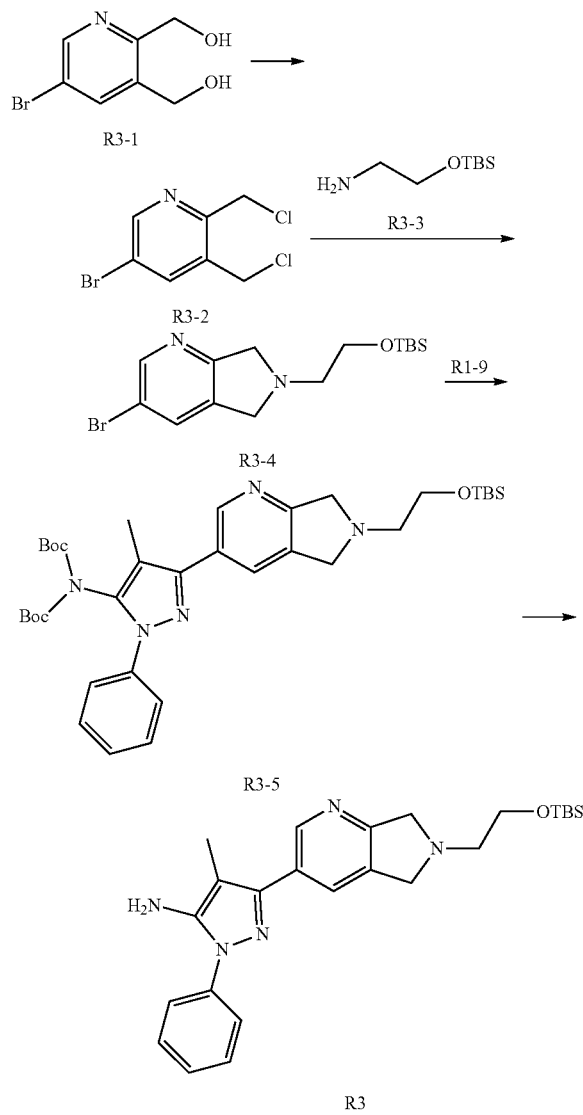

Step 1: Preparation of Compound R3-2

Under an ice-water bath, compound R3-1 (1.8 g, 8.26 mmol) was added to thionyl chloride (5.89 g, 49.53 mmol); under nitrogen atmosphere, the reaction mixture was slowly warmed to 20° C. and stirred for 16 hours. Methyl tert-butyl ether (4.75 mL) was added to the reaction mixture, and the reaction was stopped. 10 mL of methyl tert-butyl ether was additionally added, and the organic solvent was removed under reduced pressure to give crude compound R3-2, which was directly used in the next reaction without further purification. MS m/z: 256.0 [M+H]⁺.

Step 2: Preparation of Compound R3-4

Compound R3-2 (1.0 g, 3.92 mmol) was dissolved in N,N-dimethylformamide (40 mL), compound R3-3 (2.06 g, 11.76 mmol) and diisopropylethylamine (2.03 g, 15.69 mmol) were added thereto, and the reaction mixture was heated to 80° C. and stirred for 7 hours. 20 mL of water was added to the reaction mixture, and extracted with ethyl acetate (40 mL); the organic phase was dried over anhydrous sodium sulfate, filtered, and the organic solvent was removed under reduced pressure; the crude product obtained was purified by silica gel column chromatography (eluent: 0-20% EtOAc/PE) to give compound R3-4. ¹H NMR (400 MHz, CDCl₃) δ: 8.46 (s, 1H), 7.63 (s, 1H), 4.10-3.95 (m, 4H), 3.83 (t, J=6.0 Hz, 2H), 2.91 (t, J=6.0 Hz, 2H), 0.92 (s, 9H), 0.09 (s, 6H). MS m/z: 359.1 [M+H]⁺.

Step 3: Preparation of Compound R3-5

Compound R3-4 (400 mg, 1.12 mmol) and compound R1-9 (559 mg, 1.12 mmol) were dissolved in a mixed solvent of dioxane (32 mL) and water (3.2 mL); under nitrogen atmosphere, [1,1'-bis(diphenylphosphino)ferrocene]palladium dichloride (81.90 mg, 111.93 mol) and sodium carbonate (355.91 mg, 3.36 mmol) were added, and the reaction mixture was heated to 100° C. and stirred for 16 hours. The reaction mixture was cooled, filtered, and 20 mL of water was added; the mixture was extracted with ethyl acetate (30 mL×2), dried over anhydrous sodium sulfate, filtered, and the organic solvent was removed under reduced pressure; the crude product obtained was purified by thin layer chromatography on a silica gel plate (developing solvent: 100% EtOAc/PE) to give compound R₃-5. ¹H NMR (400 MHz, CDCl₃) δ: 8.78-8.74 (m, 1H), 7.96-7.89 (m, 1H), 7.60-7.44 (m, 4H), 7.40-7.34 (m, 1H), 4.13-4.09 (m, 4H), 3.89-3.84 (m, 2H), 2.96 (t, J=6.0 Hz, 2H), 2.21 (s, 1H), 2.17 (s, 2H), 1.34 (s, 18H), 0.94 (s, 9H), 0.11 (s, 6H). MS m/z: 550.4[M+H]⁺, 650.4[M+H]⁺.

Step 4: Preparation of Compound R3

Compound R3-5 (300 mg, 461.61 μmol) was dissolved in dichloromethane (30 mL), trifluoroacetic acid (10.52 g, 92.32 mmol) was added thereto, and the reaction mixture was stirred at 20° C. for 3.5 hours. 20 mL of water was added to the reaction mixture, and extracted with dichloromethane (30 mL×2); the combined organic phase was dried over anhydrous sodium sulfate, filtered, and the organic solvent was removed under reduced pressure; the crude product obtained was purified by thin layer chromatography on a silica gel plate (developing solvent: 9% MeOH/EtOAc) to give compound R4. ¹H NMR (400 MHz, CDCl₃) δ: 8.72 (s, 1H), 7.88 (s, 1H), 7.67-7.60 (m, 2H), 7.55-7.45 (m, 2H), 7.40-7.34 (m, 1H), 4.11 (s, 4H), 3.87 (t, J=6.0 Hz, 2H), 3.68 (s, 2H), 2.96 (t, J=6.4 Hz, 2H), 2.13 (s, 3H), 0.93 (s, 9H), 0.11 (s, 6H), MS m/z: 450.4 [M+H]⁺.

Reference Example 6: Synthesis of Intermediate R4

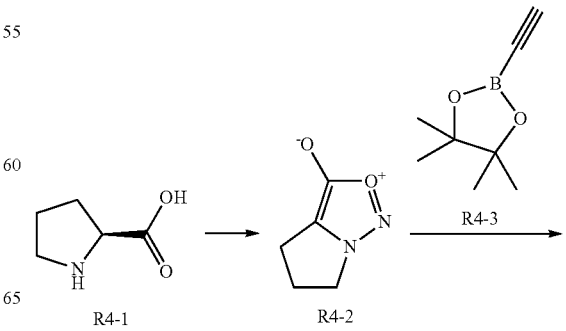

Reference Example 7: Synthesis of Intermediate R5

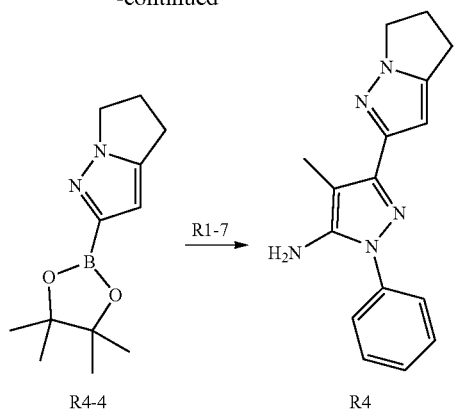

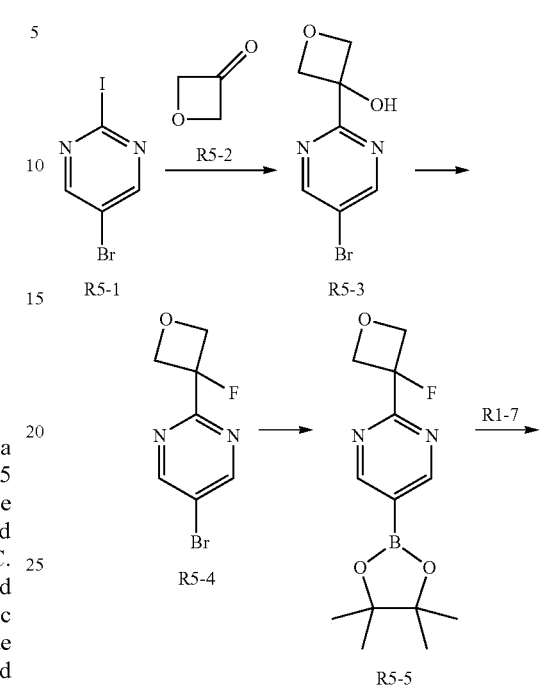

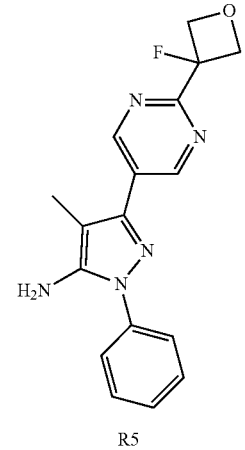

Step 1: Preparation of Compound R4-2

Compound R4-1 (15 g, 130.29 mmol) was dissolved in a mixed solvent of water (80 mL) and hydrochloric acid (15 mL); under an ice-water bath, a solution of sodium nitrite (12.58 g, 182.40 mmol) in water (30 mL) was slowly added dropwise, and the reaction mixture was warmed to 20° C. and stirred for 20 hours. The reaction mixture was extracted with ethyl acetate (150 mL×3), and the combined organic phase was washed with 300 mL of saturated sodium chloride solution, dried over anhydrous sodium sulfate, filtered, and the organic solvent was removed under reduced pressure to give a crude product, which was dispersed in toluene (50 mL); under an ice-water bath, trifluoroacetic anhydride (41.05 g, 195.43 mmol) was slowly added dropwise, and the reaction mixture was heated to 20° C. and stirred for 60 hours. The organic solvent was removed under reduced pressure, and the crude product obtained was purified by column chromatography (eluent: 30-100% EtOAc/PE) to give compound R4-2. $^1$H NMR (400 MHz, CDCl$_3$) δ: 4.42 (t, J=7.6 Hz, 2H), 2.96-2.85 (m, 2H), 2.84-2.72 (m, 2H).

Step 2: Preparation of Compound R4-4

Compound R4-2 (0.5 g, 3.96 mmol) was dissolved in 1,3,5-trimethylbenzene (5 mL), compound R4-3 (1.21 g, 7.93 mmol) was added, and the reaction mixture was heated to 160° C. and stirred for 18 hours. After cooling, the reaction mixture was filtered, and the organic solvent was removed under reduced pressure to give crude compound R$_4$-4, which was directly used in the next reaction without further purification.

Step 3: Preparation of Compound R4

Under nitrogen atmosphere, compound R4-4 (1.0 g, 4.27 mmol) and R1-7 (1.37 g, 4.27 mmol) were dissolved in a mixed solution of 1,4-dioxane (15 mL) and water (2 mL), sodium carbonate (905.50 mg, 8.54 mmol) and [1,1'-bis(diphenylphosphino)ferrocene]palladium dichloride (348.84 mg, 427.16 µmol) were added thereto, and the reaction mixture was stirred at 90° C. for 16 hours. The reaction mixture was cooled, diluted by adding 80 mL of ethyl acetate, filtered, and the organic solvent was removed under reduced pressure. The crude product obtained was purified by silica gel column chromatography (eluent: 30-80% EtOAc/PE) to give compound R4. $^1$H NMR (400 MHz, CDCl$_3$) δ: 7.73-7.29 (m, 5H), 6.36 (s, 1H), 4.21 (t, J=7.2 Hz, 2H), 3.80-3.40 (m, 2H), 2.97-2.89 (m, 2H), 2.66-2.59 (m, 2H), 2.07 (s, 3H).

Step 1: Preparation of Compound R5-3

Compound R5-1 (4.0 g, 14.04 mmol) was dissolved in tetrahydrofuran (40 mL) and cooled to −78° C., compound R5-2 (1.2 g, 16.85 mmol) was added, and then n-butyllithium (2.5 M, 8.4 mL) was slowly added dropwise; the reaction mixture was stirred at this temperature for 20 minutes. Saturated aqueous ammonium chloride solution (20 mL) was slowly added dropwise to the reaction mixture, and then extracted with ethyl acetate (50 mL×3); the combined organic phase was washed with saturated sodium chloride solution (50 mL) and dried over anhydrous sodium sulfate, filtered; the organic solvent was removed under reduced pressure, and the crude product obtained was purified by silica gel column chromatography (eluent: 0-20% EtOAc/PE) to give compound R5-3. $^1$H NMR: (400 MHz, CDCl$_3$) δ: 8.89 (s, 2H), 5.06-4.95 (m, 4H).

The following compounds were synthesized using methods similar to that for compound R5-3:

| Number of the compound | Structural formula | Spectrum |
|---|---|---|
| Compound R6-3 | 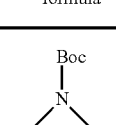 | $^1$H NMR (400 MHz, CDCl$_3$) δ: 8.86 (s, 2H), 4.38-4.36 (d, J = 8.8 Hz, 2H), 4.28-4.22 (m, 2H), 1.50 (s, 9H). |

Step 2: Preparation of Compound R5-4

Under an ice water bath, compound R5-3 (1.8 g, 7.75 mmol) was dissolved in dichloromethane (13 mL), and a solution of diethylaminosulfur trifluoride (2.5 g, 15.50 mmol) in dichloromethane (4 mL) was added; the reaction mixture was stirred at this temperature for 20 minutes. Water (20 mL) was added to the reaction mixture, and then extracted with ethyl acetate (50 mL×3); the combined organic phase was washed with saturated sodium chloride solution (50 mL), dried over anhydrous sodium sulfate, filtered, and the organic solvent was removed under reduced pressure; the crude product obtained was purified by silica gel column chromatography (eluent: 0-10% EtOAc/PE) to give compound R5-4. $^1$H NMR (400 MHz, CDCl$_3$) δ: 8.91 (s, 2H), 5.20-5.05 (m, 4H).

The following compound was synthesized using methods similar to that for compound R5-4:

| Number of the compound | Structural formula | Spectrum |
|---|---|---|
| Compound R6-4 | 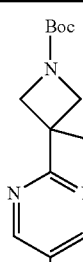 | $^1$H NMR (400 MHz, CDCl$_3$) δ: 8.89 (s, 2H), 4.59-4.49 (m, 2H), 4.46-4.34 (m, 2H), 1.49 (s, 9H). MS m/z = 275.8 [M − 56 + 1]$^+$. |

Step 3: Preparation of Compound R5-5

Compound R5-4 (300 mg, 1.29 mmol) was dissolved in 1,4-dioxane (8.0 mL), bis(pinacolato)diboron (392 mg, 1.54 mmol) and potassium acetate (379 mg, 3.86 mmol) were added successively; the reaction system was purged with nitrogen for three times, and then 1,1-bis(diphenylphosphino)ferrocene palladium dichloride (94 mg, 128.73 μmol) was added; the reaction mixture was heated to 100° C. and stirred for 11 hours. After cooling, the organic solvent was removed under reduced pressure, and the crude product obtained was purified by silica gel column chromatography (eluent: 0-50% EtOAc/PE) to give compound R5-5. $^1$H NMR (400 MHz, CDCl$_3$) δ: 9.11 (s, 2H), 5.24-5.05 (m, 4H), 1.37 (s, 12H).

The following compounds were synthesized using methods similar to that for compound R5-5:

| Number of the compound | Structural formula | Spectrum |
|---|---|---|
| Compound R6-5 | 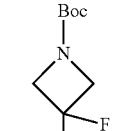 | $^1$H NMR (400 MHz, CDCl$_3$) δ: 9.10 (s, 2H), 4.61-4.53 (m, 2H), 4.46-4.37 (m, 2H), 1.49 (s, 9H), 1.39 (s, 12H). |

Step 4: Preparation of Compound R5

Compound R5-5 (320 mg, 1.14 mmol) was dissolved in a mixed solution of dioxane (2.5 mL) and water (0.5 mL), compound R1-7 (293 mg, 912.00 μmol), 1,1-bis(diphenylphosphino)ferrocene palladium dichloride (83 mg, 114.00 μmol) and sodium carbonate (242 mg, 2.28 mmol) were added successively; the reaction system was purged with nitrogen for three times, and then the reaction mixture was heated to 100° C. and stirred for 14 hours. After cooling, the reaction mixture was filtered, and the organic solvent was removed under reduced pressure; the crude product obtained was purified by silica gel column chromatography (eluent: 0-25% EtOAc/PE) to give compound R5. $^1$H NMR (400 MHz, CDCl$_3$) δ: 9.11 (s, 2H), 7.64-7.27 (m, 5H), 5.32-4.88 (m, 4H), 3.67 (s, 2H), 2.10 (s, 3H).

The following compounds were synthesized using methods similar to that for compound R5:

| Number of the compound | Structural formula | Spectrum |
|---|---|---|
| Compound R6 | 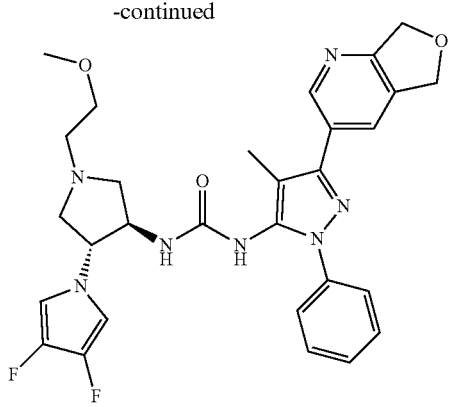 | $^1$H NMR (400 MHz, CDCl$_3$) δ: 9.18 (s, 2H), 7.67-7.62 (m, 2H), 7.55 (t, J = 8.0 Hz, 2H), 7.46-7.40 (m, 1H), 4.66-4.58 (m, 2H), 4.52-4.38 (m, 2H), 2.18 (s, 3H), 1.50 (s, 9H). MS m/z = 369.1 [M − 56 + 1]$^+$. |

Embodiment 1: Preparation of Compound 1

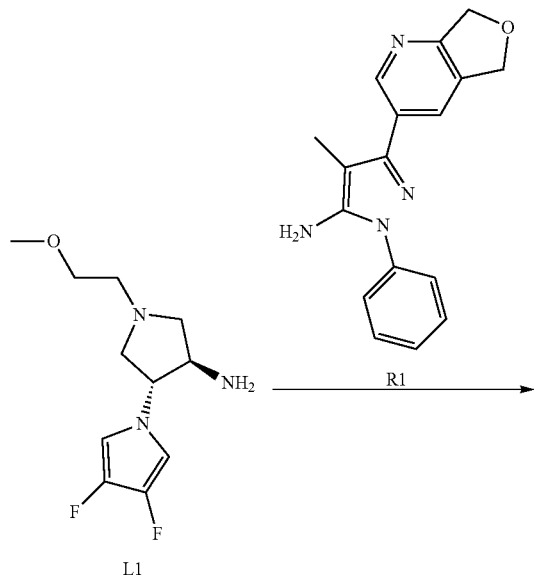

Step 1: Preparation of Compound 1

Compound R1 (40 mg, 136.83 μmol) was dissolved in dichloromethane (6 mL), triphosgene (32.48 mg, 109.46 μmol) and diisopropylethylamine (70.74 mg, 547.32 μmol) were added thereto, and the reaction mixture was stirred at 20° C. for 0.5 hour; compound L1 (35.24 mg, 143.67 μmol) and diisopropylethylamine (70.74 mg, 547.32 μmol) were added, and the reaction was continued for 3 hours. The organic solvent was removed under reduced pressure, and the crude product obtained was purified by high performance liquid chromatography (column: Xtimate C18 150*25 mm*5 m; mobile phase: [water (0 mM NH$_4$HCO$_3$)-ACN]; B %: 37%-58%, 10.5 min) to give compound 1. $^1$H NMR (400 MHz, CDCl$_3$) δ: 8.86 (s, 1H), 7.99 (s, 1H), 7.56 (d, J=7.6 Hz, 2H), 7.49 (t, J=7.2 Hz, 2H), 7.42 (t, J=7.2 Hz, 1H), 6.32 (s, 2H), 5.23 (s, 2H), 5.13 (s, 2H), 5.09-5.02 (m, 1H), 4.13 (s, 1H), 3.96 (s, 1H), 3.45 (t, J=5.2 Hz, 2H), 3.30 (s, 3H), 3.12 (t, J=10.0 Hz, 1H), 2.94 (t, J=9.6 Hz, 1H), 2.75-2.53 (m, 4H), 2.24 (s, 3H), MS m/z: 564.3 [M+H]$^+$.

The following compounds were synthesized using methods similar to that for compound 1:

| Embodiment | Number of the compound | Structural formula | Spectrum |
|---|---|---|---|
| 2 | Compound 2 | 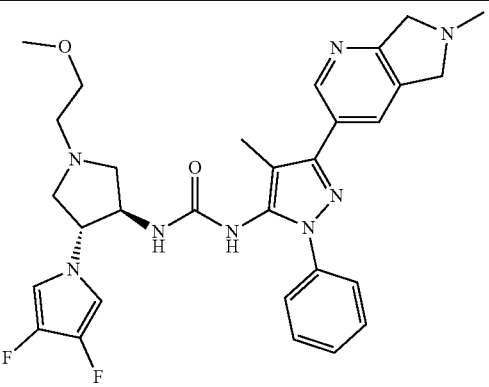 | $^1$H NMR (400 MHz, CDCl$_3$) δ: 8.76 (s, 1H), 7.92 (s, 1H), 7.60-7.54 (m, 2H), 7.53-7.47 (m, 2H), 7.44-7.36 (m, 1H), 6.33 (s, 2H), 5.06 (s, 1H), 4.16 (s, 1H), 4.06-3.98 (m, 4H), 3.98-3.91 (m, 1H), 3.45 (t, J = 5.2 Hz, 2H), 3.30 (s, 3H), 3.11 (t, J = 8.4 Hz, 1H), 2.95 (t, J = 9.6 Hz, 1H), 2.70- 2.50 (m, 7H), 2.21 (s, 3H). MS m/z: 577.4 [M + H]$^+$. |
| 3-1 | Intermediate 3-1 | 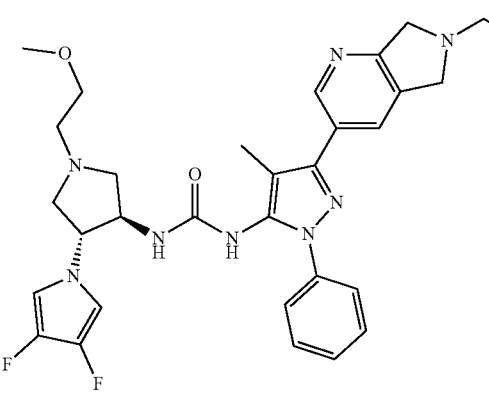 | MS m/z: 721.4 [M + H]$^+$. |
| 4 | Compound 4 | 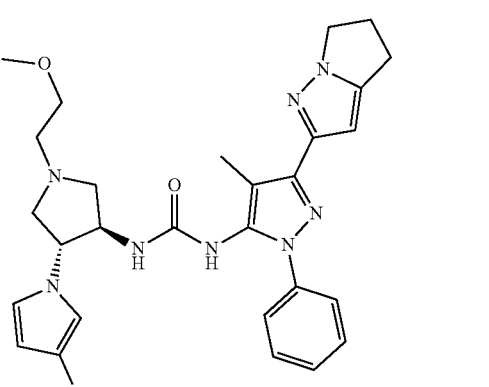 | $^1$H NMR (400 MHz, CD$_3$OD) δ: 7.57-7.40 (m, 5H), 6.60 (s, 1H), 6.52 (s, 1H), 6.40 (s, 1H), 5.87-5.78 (m, 1H), 4.64 (s, 1H), 4.33-4.15 (m, 4H), 3.52 (t, J = 5.2 Hz, 2H), 3.36 (s, 3H), 3.14-3.03 (m, 2H), 2.97 (t, J = 7.2 Hz, 2H), 2.86- 2.80 (m, 1H), 2.77-2.63 (m, 4H), 2.55-2.42 (m, 1H), 2.19 (s, 3H). MS m/z = 533.4 [M + 1]$^+$. |
| 5 | Compound 5 | 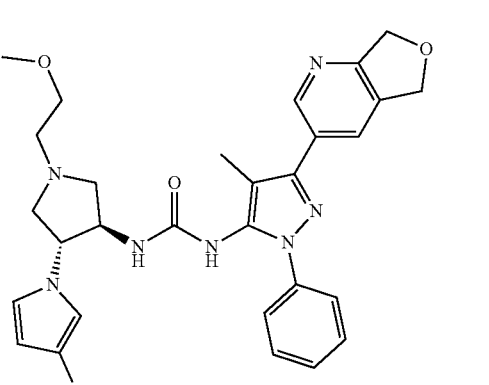 | $^1$H NMR (400 MHz, CD$_3$OD) δ: 8.81 (s, 1H), 8.11 (s, 1H), 7.62-7.41 (m, 5H), 6.62 (s, 1H), 6.53 (d, J = 3.6 Hz, 1H), 5.85-5.80 (m, 1H), 5.24 (s, 2H), 5.08 (s, 2H), 4.33-4.17 (m, 2H), 3.53 (t, J = 5.2 Hz, 2H), 3.37 (s, 3H), 3.16-3.05 (m, 2H), 2.84-2.75 (m, 1H), 2.79-2.64 (m, 2H), 2.56-2.48 (m, 1H), 2.18 (s, 3H). MS m/z = 546.4 [M + 1]$^+$. |

-continued
| Embodiment | Number of the compound | Structural formula | Spectrum |
|---|---|---|---|
| 6 | Compound 6 | 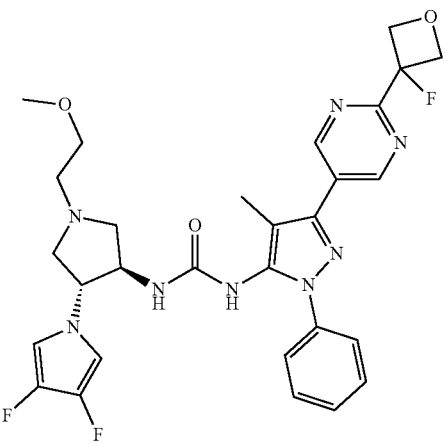 [SMILES: COCCN1C[C@@H](n2cc(F)c(F)c2)[C@H](NC(=O)Nc2c(C)c(-c3cnc(C4(F)COC4)nc3)nn2-c2ccccc2)C1] | ¹H NMR (400 MHz, CDCl₃) δ: 9.22 (s, 2H), 7.58-7.44 (m, 5H), 6.32 (s, 2H), 5.35-5.05 (m 4H), 4.20-3.86 (m, 2H), 3.50-3.40 (m, 2H), 3.28 (s, 3H), 3.16 (t, J = 9.2 Hz, 1H), 2.91 (t, J = 8.8 Hz, 1H), 2.72-2.57 (m, 4H), 2.25 (s, 3H). MS m/z: 597.5 [M + H]⁺. |
| 7 | Compound 7 | 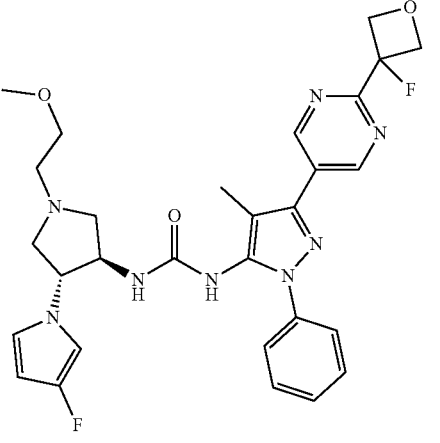 [SMILES: COCCN1C[C@@H](n2ccc(F)c2)[C@H](NC(=O)Nc2c(C)c(-c3cnc(C4(F)COC4)nc3)nn2-c2ccccc2)C1] | ¹H NMR (400 MHz, CD₃OD) δ: 9.28 (s, 2H), 7.67-7.40 (m, 5H), 6.66-6.49 (m, 2H), 5.84 (s, 1H), 5.33-5.20 (m, 2H), 5.14-5.00 (m, 2H), 4.34-4.16 (m, 2H), 3.53 (t, J = 5.2 Hz, 2H), 3.37 (s, 3H), 3.17-3.05 (m, 2H), 2.87-2.78 (m, 1H), 2.79-2.63 (m, 2H), 2.58-2.47 (m, 1H), 2.23 (s, 3H), MS m/z = 579.4 [M + 1]⁺. |

Embodiment 3: Preparation of Compound 3

Embodiment 8: Preparation of Compound 8

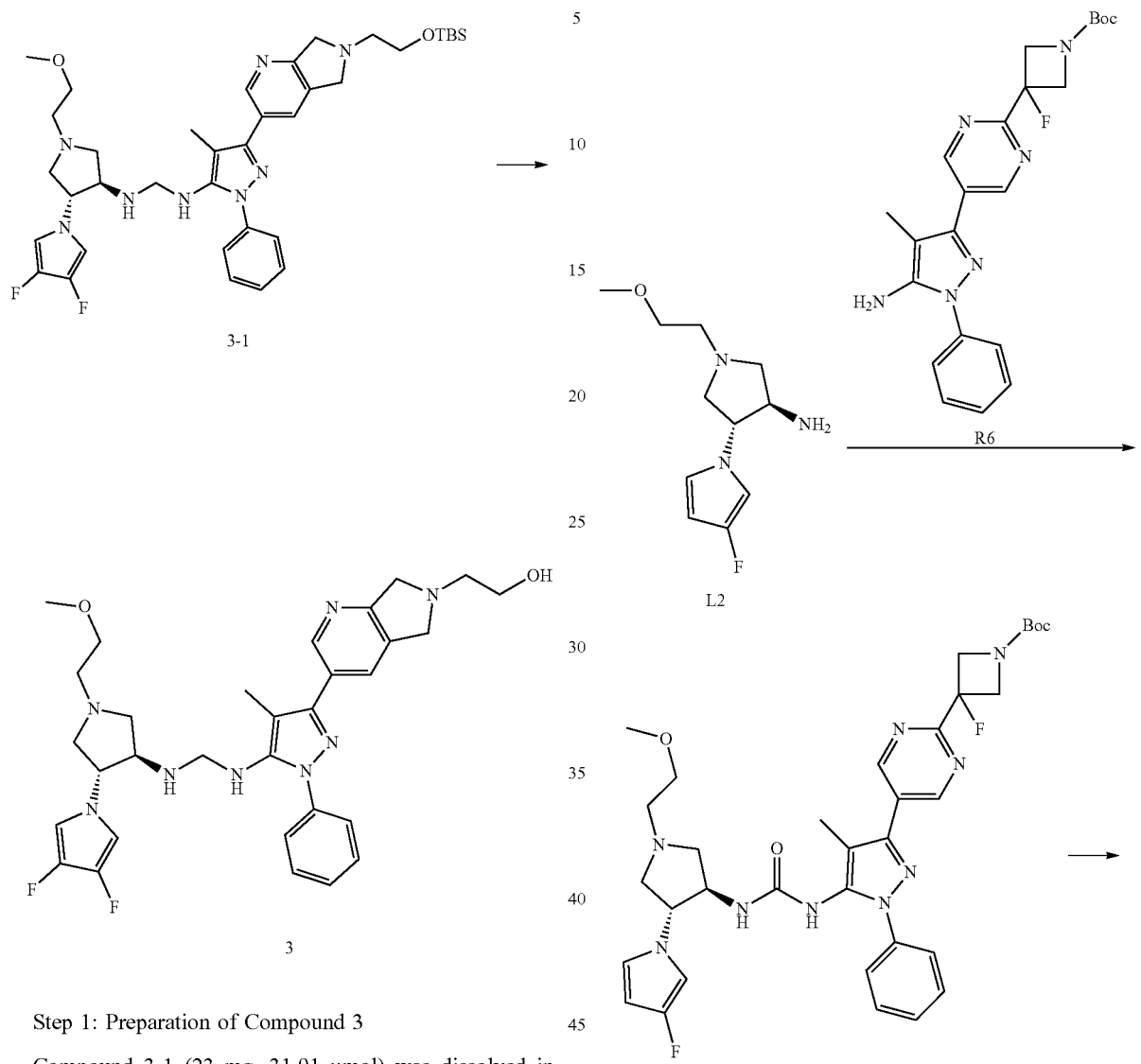

Step 1: Preparation of Compound 3

Compound 3-1 (23 mg, 31.91 μmol) was dissolved in tetrahydrofuran (6 mL), tetrabutylammonium fluoride (1 M, 95.71 μL) was added thereto, and the reaction mixture was heated to 50° C. and stirred for 2 hours. The reaction mixture was cooled and the organic solvent was removed under reduced pressure. The crude product obtained was purified by high performance liquid chromatography (column: Waters Xbridge 150*25 mm 5 m; mobile phase: [water (10 mM NH$_4$HCO$_3$)-ACN]; B %: 30%-40%, 12 min) to give compound 3. $^1$H NMR (400 MHz, CDCl$_3$) δ: 8.61 (s, 1H), 7.72 (d, J=9.2 Hz, 3H), 7.50 (t, J=7.6 Hz, 2H), 7.38 (t, J=14.8 Hz, 1H), 6.47 (s, 2H), 4.22 (d, J=19.6 Hz, 2H), 4.00-3.84 (m, 1H), 3.77 (m, 2H), 3.64 (s, 2H), 3.54 (s, 3H), 3.43 (s, 3H), 3.30-3.24 (m, 1H), 2.89-2.72 (d, J=31.2 Hz, 6H), 2.51 (s, 1H), 1.90 (s, 3H), MS m/z: 607.3[M+H]$^+$.

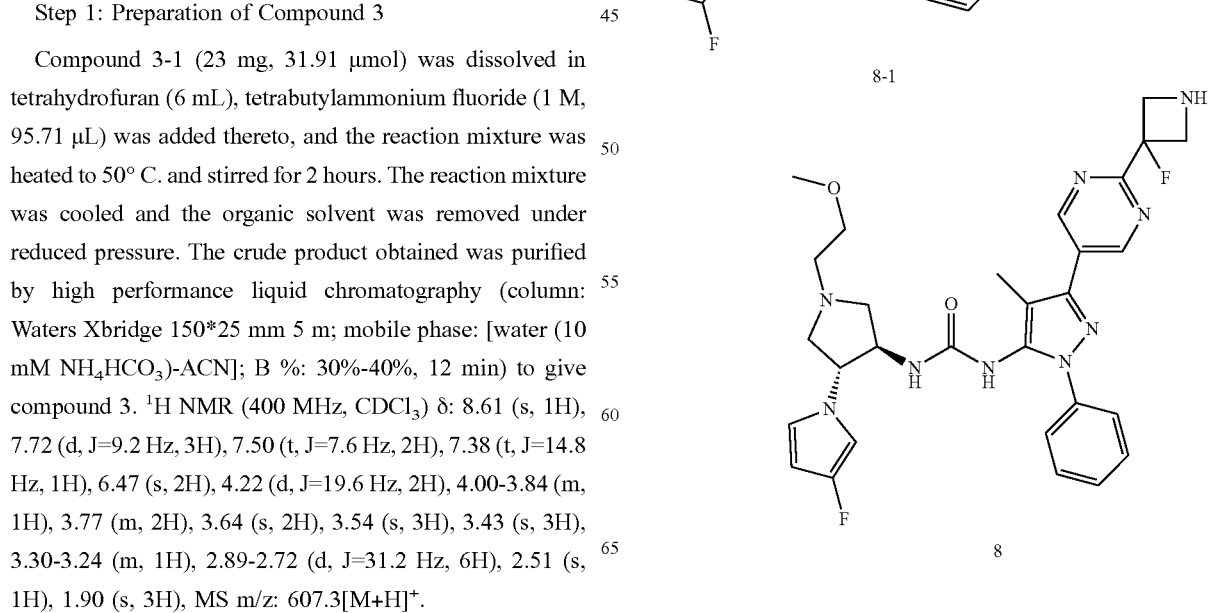

Step 1: Preparation of Compound 8-1

Compound R6 (250 mg, 588.97 μmol) was dissolved in dichloromethane (10 mL), triphosgene (174.78 mg, 588.97 μmol) was added, and N,N-diisopropylethylamine (228.36 mg, 1.77 mmol, 307.76 μL) was added dropwise; the reaction mixture was stirred at 25° C. for 20 minutes; then compound L2 (446.20 mg, 588.97 μmol) and N,N-diisopropylethylamine (228.36 mg, 1.77 mmol, 307.76 μL) were added thereto, and the reaction mixture was then stirred for 18 hours. 20 mL of water was added to the reaction mixture, and the mixture was partitioned; the aqueous phase was extracted with dichloromethane (30 mL*2); the extracted organic phases were combined, washed with 30 mL of saturated brine, dried over anhydrous sodium sulfate, and filtered; the organic solvent was removed under reduce pressure, and the crude product obtained was purified by column chromatography (eluent: 30-60% EtOAc/PE to 10% MeOH/DCM) to give compound 8-1, which was used directly in the next reaction without further purification. MS m/z: 678.6 [M+1]$^+$.

Step 2: Preparation of Compound 8

Compound 8-1 (80 mg, 118.04 μmol) was dissolved in dichloromethane (20 mL), trifluoroacetic acid (0.5 mL) was added thereto, and the reaction mixture was stirred for 1 hour. The organic solvent was removed under reduced pressure, and the crude product obtained was purified by high performance liquid chromatography (column: Waters Xbridge 150*25 mm*5 m, mobile phase: [water (10 mM ammonium carbonate)-acetonitrile]; B %: 20%-50%, 8 min) to give compound 8. $^1$H NMR (400 MHz, CD$_3$OD) δ: 9.27 (s, 2H), 7.69-7.39 (m, 5H), 6.62 (s, 1H), 6.53 (s, 1H), 5.83 (s, 1H), 4.44-4.06 (m, 6H), 3.56-3.50 (m, 2H), 3.37 (s, 3H), 3.15-3.05 (m, 2H), 2.89-2.81 (m, 1H), 2.77-2.65 (m, 2H), 2.56-2.50 (m, 1H), 2.23 (s, 3H). MS m/z: 578.5 [M+1]*.

Embodiment 9: Preparation of Compound 9

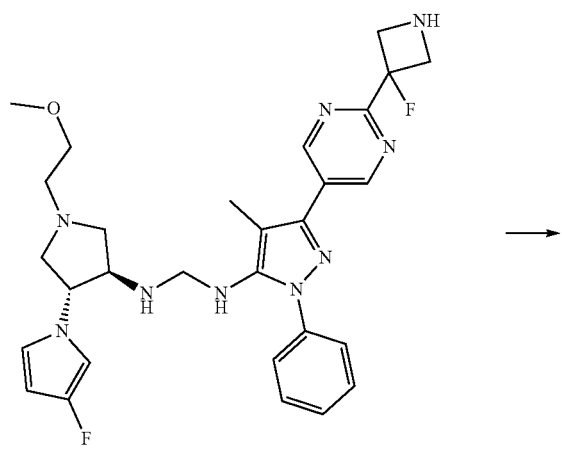

8

-continued

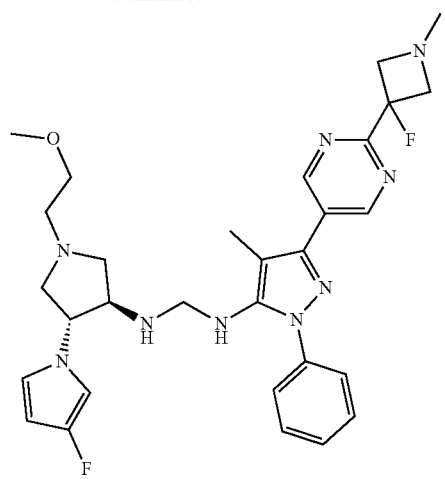

9

Step 1: Preparation of Compound 9

Compound 8 (110.38 mg, 191.09 μmol) was dissolved in methanol (8 mL), aqueous formaldehyde solution (3.26 g, 40.13 mmol, 2.99 mL) and glacial acetic acid (0.1 mL) were added, and sodium triacetoxyborohydride (81.00 mg, 382.18 μmol) was added; the reaction mixture was stirred at 25° C. for 17 hours, then sodium triacetoxyborohydride (81.00 mg, 382.18 μmol) was added and the mixture was stirred for 1 hour. The organic solvent was removed under reduced pressure, and the crude product obtained was purified by high performance liquid chromatography (column: Waters Xbridge 150*25 mm*5 m, mobile phase: [water (10 mM ammonium carbonate)-acetonitrile]; B %: 22%-52%, 8 min) to give compound 9. $^1$H NMR (400 MHz, CD$_3$OD) δ: 9.26 (s, 2H), 7.69-7.42 (m, 5H), 6.64-6.60 (m, 1H), 6.55-6.51 (m, 1H), 5.86-5.80 (m, 1H), 4.60 (brs, 1H), 4.34-4.19 (m, 2H), 4.14-4.06 (m, 2H), 3.87-3.74 (m, 2H), 3.53 (t, J=5.2 Hz, 2H), 3.37 (s, 3H), 3.17-3.06 (m, 2H), 2.86-2.82 (m, 1H), 2.78-2.63 (m, 2H), 2.54 (s, 3H), 2.53-2.47 (m, 1H), 2.23 (s, 3H). MS m/z=592.5 [M+1]$^+$.

Embodiment 10: Synthesis of Reference Compound D1

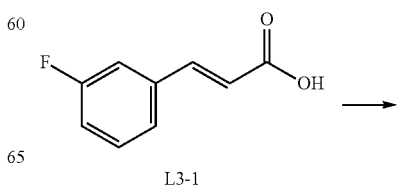

L3-1

-continued

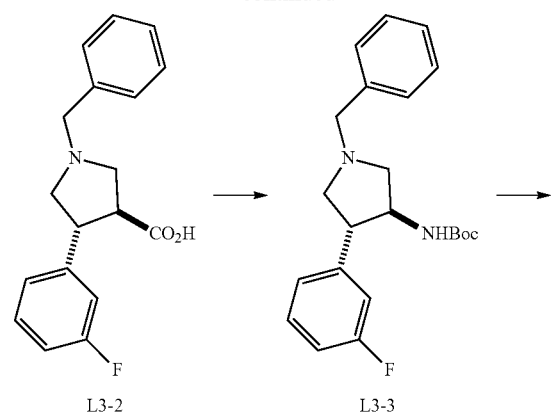

L3-2 → L3-3

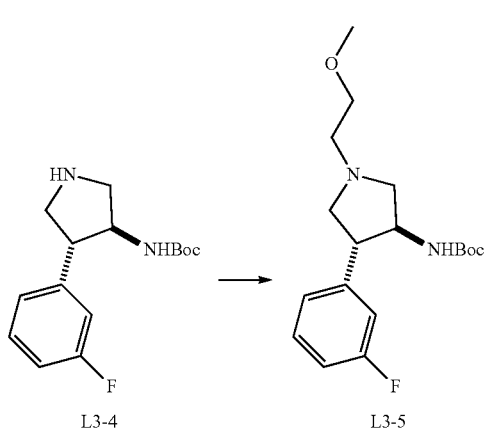

L3-4 → L3-5

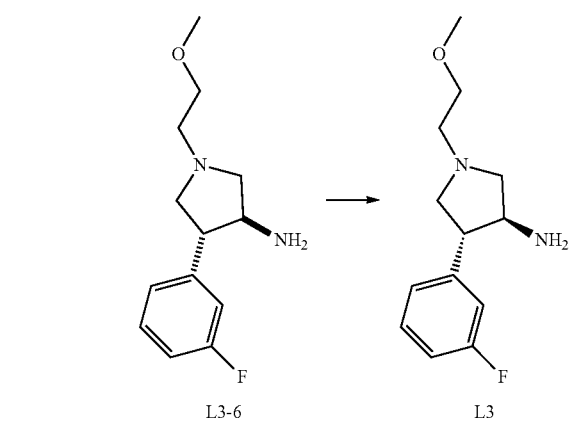

L3-6 → L3

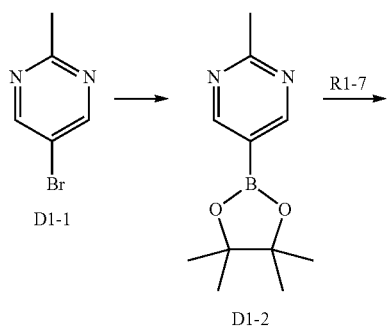

D1-1 → D1-2 →R1-7

-continued

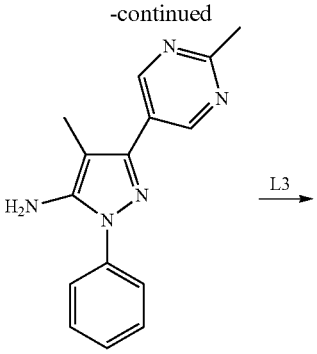

D1-3 →L3

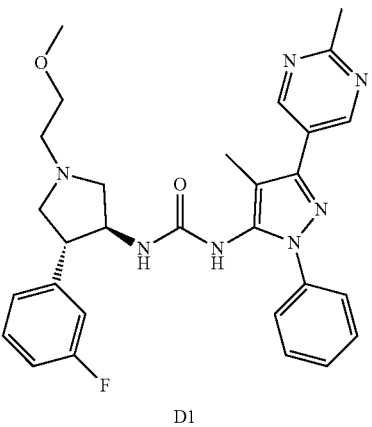

D1

Step 1: Preparation of Compound L3-2

Compound L3-1 (38.50 g, 231.7 mmol) was dissolved in a mixed solvent of ethyl acetate (200.0 mL) and n-heptane (200.0 mL), trifluoroacetic acid (2.64 g, 23.2 mmol, 1.7 mL) was added; under an ice-water bath, N-(methoxymethyl)-N-(trimethylsilylmethyl)benzylamine (137.53 g, 579.3 mmol) was slowly added dropwise, and the reaction mixture was slowly warmed to 25° C. and stirred for 20 hours. The reaction mixture was concentrated to about 300.0 mL, then 300 mL of n-heptane was added; the resulting mixture was concentrated again to about 300.0 mL; the above operation was repeated for 6 times, until the last addition of 300 mL of n-heptane. The mixture was filtered, and the filter cake was washed with n-heptane (100.0 mL×2) twice to give crude compound L3-2, which was directly used in the next reaction without further purification. $^1$H NMR (400 MHz, CDCl$_3$) δ: 7.45-4.43 (m, 2H), 7.37-7.21 (m, 4H), 7.13-6.98 (m, 2H), 6.95-6.85 (m, 1H), 4.51 (d, J=12.4 Hz, 1H), 4.16-3.99 (m, 2H), 3.78 (d, J=12.4 Hz, 1H), 3.49 (t, J=10.0 Hz, 1H), 3.20-3.10 (m, 2H), 2.75 (t, J=10.0 Hz, 1H).

Step 2: Preparation of Compound L3-3

Under nitrogen atmosphere, L3-2 (53.00 g, 177.06 mmol) was dissolved in toluene (400.0 mL), diisopropylethylamine (25.17 g, 194.77 mmol, 34.0 mL) was added; under nitrogen atmosphere, diphenylphosphoryl azide (53.60 g, 194.77 mmol, 42.2 mL) was slowly added dropwise; the reaction mixture was stirred at 25° C. for 0.5 hour, heated to 90° C. and stirred for 3 hours; tert-butanol (80.0 mL) was added, and the reaction mixture was stirred at this temperature for 16 hours. The mixture was cooled, and 500.0 mL of saturated sodium bicarbonate solution was added, and extracted twice with ethyl acetate (600.0 mL×2); the combined organic phase was washed with saturated brine (800.0 mL), dried over anhydrous sodium sulfate, filtered, and the organic solvent was removed under reduced pressure; the crude product obtained was purified by silica gel column chromatography (eluent: 0-10% EtOAc/PE) to give compound L3-3. $^1$H NMR (400 MHz, CDCl$_3$) δ: 7.27-7.25 (m, 4H), 7.21-7.15 (m, 2H), 7.01-6.89 (m, 2H), 6.86-6.80 (m, 1H), 4.84 (br s, 1H), 4.11 (br s, 1H), 3.57 (s, 2H), 3.15-2.94 (m, 2H), 2.90-2.82 (m, 1H), 2.68-2.58 (m, 1H), 2.44-2.34 (m, 1H), 1.39 (s, 9H).

Step 3: Preparation of Compound L3-4

Under nitrogen atmosphere, L3-3 (29.40 g, 79.36 mmol) was dissolved in a mixed solvent of methanol (300.0 mL) and tetrahydrofuran (75.0 mL), palladium on carbon (3.00 g, purity 10%) was added thereto, and the reaction mixture was stirred at 25° C. for 18 hours under 50 psi hydrogen. The reaction mixture was filtered through diatomite and the organic solvent was removed under reduced pressure to give compound L3-4, which was directly used in the next reaction without further purification. $^1$H NMR (400 MHz, CDCl$_3$) δ: 7.33-7.26 (m, 1H), 7.05 (d, J=7.6 Hz, 1H), 7.01-6.96 (m, 1H), 6.96-6.90 (m, 1H), 4.92 (br s, 1H), 4.18-4.02 (m, 1H), 3.47-3.36 (m, 2H), 3.17-2.84 (m, 3H), 1.41 (s, 9H). MS m/z: 281.1 [M+1]$^+$.

Step 4: Preparation of compound L3-5

L3-4 (14.50 g, 51.72 mmol) was dissolved in N,N-dimethylformamide (100.0 mL), diisopropylethylamine (20.05 g, 155.16 mmol, 27.1 mL) and 2-bromoethyl methyl ether (8.63 g, 62.06 mmol, 5.8 mL) were successively added, and the reaction mixture was stirred at 25° C. for 16 hours. The reaction mixture was diluted by adding 400.0 mL of water, and extracted with ethyl acetate (400.0 mL×3); the combined organic phase was washed with saturated brine (800.0 mL×2), dried over anhydrous sodium sulfate, filtered, and the organic solvent was removed under reduced pressure. 200.0 mL of petroleum ether was added to the crude product obtained, filtered, and the filter cake was collected to give compound L3-5, which was directly used in the next reaction without further purification. $^1$H NMR (400 MHz, CDCl$_3$) δ: 7.30-7.25 (m, 1H), 7.08 (d, J=7.6 Hz, 1H), 7.01 (d, J=10.0 Hz, 1H), 6.95-6.90 (m, 1H), 4.98 (br s, 1H), 4.21 (br s, 1H), 3.53 (t, J=5.6 Hz, 2H), 3.39 (s, 3H), 3.35-3.31 (m, 1H), 3.15-3.11 (m, 1H), 2.90-2.80 (m, 2H), 2.81-2.65 (m, 2H), 2.51-2.39 (m, 1H), 1.43 (s, 9H). MS m/z: 339.2 [M+1]$^+$.

Step 5: Preparation of compound L3-6

L3-5 (16.50 g, 48.76 mmol) was suspended in ethyl acetate (50.0 mL), hydrochloric acid/ethyl acetate (4.0 M, 50.0 mL) was added, and the reaction was allowed to run at 25° C. for 0.5 hour. The reaction mixture was concentrated to dryness, and 15% sodium hydroxide solution (50.0 mL) was added to the crude product obtained; the aqueous phase was extracted three times with dichloromethane (60.0 mL×3); the organic phases were combined and dried over anhydrous sodium sulfate, filtered, and the filtrate was concentrated to dryness to give 11.40 g of crude compound L3-6. MS m/z=239.1 [M+1]$^+$.

Step 6: Preparation of Compound L3

Compound L3-6 (11.40 g, 47.84 mmol) was dissolved in a mixed solvent of methanol (99.0 mL) and water (11.0 mL), and then D-(+)-di-p-toluoyl-tartaric acid (20.33 g, 52.62 mmol) was added; the reaction mixture was heated to 50° C. and stirred for 1 hour, then slowly cooled to room temperature, and allowed to stand for 16 hours. The reaction mixture was filtered, and the filter cake was washed with ethyl acetate (30.0 mL×2); the filter cake was collected and suspended in 15% sodium hydroxide solution (100.0 mL), extracted with ethyl acetate (60.0 mL×3); the combined organic phase was washed once with saturated sodium chloride solution (150.0 mL), dried over anhydrous sodium sulfate, and filtered; the organic solvent was removed under reduced pressure to give compound L3, which was directly used in the next reaction without further purification. $^1$H NMR (400 MHz, CDCl$_3$) δ: 7.31-7.24 (m, 1H), 7.06 (d, J=7.6 Hz, 1H), 7.03-7.00 (m, 1H), 6.95-6.88 (m, 1H), 3.52 (t, J=5.6 Hz, 2H), 3.48-3.42 (m, 1H), 3.38 (s, 3H), 3.22-3.15 (m, 1H), 3.05-2.90 (m, 2H), 2.83-2.73 (m, 1H), 2.72-2.61 (m, 3H). MS m/z: 239.1 [M+1]$^+$. SFC: chromatographic column: Lux Cellulose-2 (150 mm*4.6 mm, 3 m); mobile phase: [0.1% ethanolamine-methanol]; B %: 5%-40% 5.5 min, 40% 3 min, 5% 1.5 min; Rt=4.889 min; 97.7% ee.

Step 7: Preparation of Compound D1-2

Compound D1-1 (5.00 g, 28.90 mmol) was dissolved in 1,4-dioxane (120.0 mL), and bis(pinacolato)diboron (8.81 g, 34.68 mmol) and potassium acetate (5.67 g, 57.80 mmol) were added successively; under nitrogen atmosphere, 1,1-bis(diphenylphosphino)ferrocene palladium dichloride (1.06 g, 1.45 mmol) was added, and the reaction mixture was heated to 100° C. and stirred for 18 hours. After cooling, the reaction mixture was filtered, and the organic solvent was removed under reduced pressure; the crude product obtained was purified by silica gel column chromatography (eluent: 0-50% EtOAc/PE) to give compound D1-2, which was directly used in the next step without further purification. $^1$H NMR (400 MHz, CDCl$_3$) δ: 8.92 (s, 2H), 2.75 (s, 3H), 1.35 (s, 12H).

Step 8: Preparation of Compound D1-3

Compound D1-2 (2.67 g, 12.14 mmol) was dissolved in a mixed solvent of ethanol (15.0 mL) and toluene (45.0 mL), and then compound R1-7 (3.00 g, 9.34 mmol) and sodium carbonate (1.98 g, 18.68 mmol) were added thereto; under nitrogen atmosphere, tetrakis(triphenylphosphine)palladium (1.08 g, 933 μmol) was added, and the reaction mixture was heated to 100° C. and stirred for 17 hours. After cooling, the reaction mixture was filtered, and the filter cake was washed with ethyl acetate (50.0 mL); the filtrates were combined, and the organic solvent was removed under reduced pressure; the crude product obtained was purified by silica gel column chromatography (eluent: 0-100% EtOAc/PE) to give compound D1-3. $^1$H NMR (400 MHz, CDCl$_3$) δ: 8.99 (s, 2H), 7.65-7.60 (m, 2H), 7.56-7.50 (m 2H), 7.43-7.37 (m, 1H), 3.71 (s, 2H), 2.79 (s, 3H), 2.14 (s, 3H). MS m/z: 266.0 [M+1]$^+$.

Step 9: Preparation of Compound D1

Compound D1-3 (500 mg, 1.88 mmol) was dissolved in dichloromethane (6.0 mL), and then diisopropylethylamine (972 mg, 7.52 μmol, 1.3 mL) and triphosgene (390 mg, 1.32 mmol) were added thereto; the reaction mixture was stirred at 25° C. for 20 minutes, and compound L3 (448 mg, 1.88 mmol) and diisopropylethylamine (972 mg, 7.52 mmol, 1.3 mL) were added successively; then the reaction mixture was stirred at 25° C. for 17 hours. The reaction mixture was diluted by adding dichloromethane (30.0 mL), and the organic phase was washed with saturated brine (30.0 mL), dried over anhydrous sodium sulfate, and filtered; the organic solvent was removed under reduced pressure, and the crude product obtained was purified by silica gel column chromatography (eluent: 0-100% EtOAc/PE) to give compound DL. $^1$H NMR (400 MHz, METHANOL-d$_4$) δ: 8.91 (s, 2H), 7.45-7.23 (m, 6H), 7.11-6.91 (m, 3H), 4.50-4.38 (m, 1H), 3.86-3.75 (m, 1H), 3.70-3.47 (m, 6H), 3.36 (s, 3H), 3.24-3.06 (m, 3H), 2.63 (s, 3H), 2.00 (s, 3H). MS m/z: 530.1 [M+1]$^+$.

| Experimental Materials | TrkA enzyme activity test |
|---|---|
| TrkA | Invitrogen-PV4114 |
| TK detection kit | Cisbio-62TK0PEJ |
| Test plate | PerkinElmer-6007299 |
| Envision | PerkinElmer-2104 |

Kinase Reaction Buffer 50 mM Hepes (pH 7.5), 5 mM $MgCl_2$ (magnesium chloride), 0.01 mM orthovanadate (sodium vanadate), 1% BSA (bovine serum albumin), 1 mM (dithiothreitol)

Experimental Method

This experiment used Cisbio's homogeneous time-resolved fluorescence resonance energy transfer (HTRF® method) for activity test. In the test plate, the enzyme, biotin-labeled peptide substrate, ATP, and test compound were mixed, and incubated for reaction. After the reaction, ethylenediaminetetraacetic acid was added to terminate the reaction; at the same time, Eu-labeled antibody and streptavidin-labeled XL665 were added for reaction and detection. The data were expressed by the readings of the fluorescence signal at 665 nm and 620 nm, where a high ratio of 665 nm/620 nm indicated higher activity, and a low ratio of 665 nm/620 nm indicated inhibition of activity.

Experimental Operation

1. Dilution of compound: the test compound was 3-fold diluted to prepare a total of 11 concentrations, the concentration was from 10 μM to 0.17 nM in the final system;

2. A 10 μL reaction system with a buffer of 50 mM Hepes (pH 7.5), 5 mM $MgCl_2$, 0.01 mM sodium vanadate, 1% BSA, and 1 mM DTT, and containing 0.5 nM TrkA kinase, 0.3 μM biotin-TK peptide (biotin-labeled tyrosine kinase substrate peptide), 90 μM ATP was incubated at 23° C. for 90 minutes. 10 μL of stop solution containing 20 mM EDTA, 1.34 nM phosphorylated substrate antibody, and 100 nM streptavidin-labeled fluorescent molecule XL-665 was then added, incubated at 23° C. for 60 minutes; the signal was read with Envision;

3. The inhibition rate of the compound was calculated from the data read by the instrument, and the $IC_{50}$ value was calculated using the mode 205 in XLFIT5 of IDBS.

Experimental Results

The results are shown in Table 1.

TABLE 1

$IC_{50}$ value of the compounds inhibiting TrkA enzyme

| Number of the compound | TrkA $IC_{50}$ (nM) |
|---|---|
| Compound 1 | 0.16 |
| Compound 2 | 0.27 |
| Compound 3 | 0.25 |
| Compound 4 | 3.05 |
| Compound 5 | 0.24 |
| Compound 6 | 0.27 |
| Compound 7 | 0.56 |
| Compound 8 | 1.03 |
| Compound 9 | 0.92 |

The results show that the compounds of the present disclosure have a significant inhibitory effect on TrkA enzyme.

Plasma Protein Binding Rate (PPB) Test

Experimental Objective

The protein binding rates of the test compound in the plasma of humans, SD rats and Beagle dogs were determined.

Experimental Operation

796 μL of blank plasma from humans, SD rats and Beagle dogs (plasma purchased from BioreclamationIVT) were taken, 4 μL of working solution of the test compound (400 μM) or warfarin working solution (400 μM) was added and the final concentration of the test compound or warfarin was 2 μM. The sample was mixed thoroughly. The final concentration of organic phase DMSO was 0.5%; 50 μL of the plasma sample treated with the test compound or warfarin was pipetted into the sample receiving plate, and a corresponding volume of blank plasma or buffer was added immediately so that the final volume in each sample well was 100 μL, the volume ratio of plasma:dialysis buffer was 1:1; 400 μL of stop solution was added to these samples, and these samples were used as $T_0$ samples for recovery and stability determination. To samples were stored at 2° C. to 8° C. for subsequent processing together with other dialyzed samples; 150 μL of the plasma sample treated with the test compound or warfarin was added into the dosing end of each dialysis hole, and 150 μL of blank dialysis buffer was added to the receiving end corresponding to the dialysis hole. Then the dialysis plate was sealed with gas-permeable membrane and placed in a humidified 5% $CO_2$ incubator, and incubated at 37° C. with 100 rpm shaking for 4 hours. After the dialysis, 50 μL of the dialysis buffer sample and the dialysis plasma sample was transferred to a new sample receiving plate. A corresponding volume of blank plasma or buffer was added to the sample, so that the final volume was 100 μL in each sample well, and the volume ratio of plasma:dialysis buffer was 1:1. All samples were analyzed by LC/MS/MS after protein precipitation, and the plasma protein unbound rate, binding rate and recovery rate was calculated according to the following formula: % unbound rate=100*free compound concentration at the membrane buffer side/total compound concentration at the membrane plasma side, % protein binding rate=100-% unbound rate, % recovery rate=100*(free compound concentration at the membrane buffer side+total compound concentration at the membrane plasma side)/total compound concentration before dialysis.

Experimental Results

The results are shown in Table 2.

TABLE 2

Human and rat plasma protein unbound rate of compounds D1, 2, 3 and 7

| | Plasma protein unbound rate | |
|---|---|---|
| Number of the compound | Human plasma | SD Rat plasma |
| Reference compound D1 | 13.6% | 9.6% |
| Compound 2 | 15.3% | 5.1% |
| Compound 3 | 33.8% | 8.0% |
| Compound 7 | 13.2% | 7.1% |

The results show that the compounds of the present disclosure have a plasma protein unbound rate comparable to that of the reference compound D1.

Cytochrome P450 Isozyme Inhibitory Activity Test

Experimental Objective

Determination of the inhibitory activity of the test compound on different human cytochrome P450 isozymes.

Experimental Operation

The test compound, standard inhibitor (100×final concentration), and a mixed substrate working solution were prepared; the microsome frozen in −80° C. refrigerator was thawed. 2 µL of the test compound and standard inhibitor solution was added to the corresponding wells, and at the same time 2 µL of the corresponding solvent was added to the non-inhibitor control wells (NIC) and blank control wells (Blank) wells; then 20 µL of mixed substrate solution was added to the corresponding wells, except for the Blank wells (20 µL of PB was added to the Blank wells); a human liver microsome solution was prepared (put back into the refrigerator immediately after using and marking the date), and then 158 µL of the human liver microsome solution was added to all wells; the above sample plate was placed in a 37° C. water bath for pre-incubation, then the coenzyme factor (NADPH) solution was prepared; 10 minutes later, 20 µL of the NADPH solution was added to all wells, and the sample plate was shaken well, placed in a 37° C. water bath and incubated for 10 minutes; at the corresponding time point, 400 µL of cold acetonitrile solution (internal standard: 200 ng/mL tolbutamide and labetalol) was added to terminate the reaction; the sample plate was evenly mixed, centrifuged at 4000 rpm for 20 minutes to precipitate proteins; 200 µL of the supernatant was added to 100 µL of water, shook well, and tested by LC/MS/MS.

Experimental Results

The results are shown in Table 3.

TABLE 3

$IC_{50}$ value of compounds D1, 1 and 7 for P450 isozyme inhibition

| Number of the compound | Cytochrome P450 isozyme $IC_{50}$ (nM) | | | | |
|---|---|---|---|---|---|
| | CYP1A2 | CYP2C9 | CYP2C19 | CYP2D6 | CYP3A4 |
| Reference compound D1 | >50 | >50 | >50 | 39.7 | 37.1 |
| Compound 1 | >50 | 24.2 | >50 | 28.5 | 19.2 |
| Compound 7 | >50 | 39.1 | >50 | 40.6 | >50 |

The results show that the compounds of the present disclosure have a lower risk of drug-drug interaction.

Metabolic Stability (MMS) Study by Liver Microsome

Experimental Objective

Determination of the metabolic stability of the test compound by human, rat and canine liver microsome.

Experimental Materials

Test compound (10 mM), testosterone (reference compound, 10 mM), diclofenac (reference compound, 10 mM), propafenone (reference compound, 10 mM).

Buffer System 100 mM potassium phosphate buffer (pH 7.4).

10 mM $MgCl_2$.

Dilution of Compound

Intermediate solution: 45 µL of DMSO was used (with 450 µL of 1:1 methanol/water) to dilute 5 µL of the test or reference compound.

Working solution: 450 µL of 100 mM potassium phosphate buffer was used to dilute the intermediate solution.

NADPH Regeneration System

1. β-Nicotinamide adenine dinucleotide phosphate, from Sigma, Cat. No. N0505.

2. Isocitrate, from Sigma, Cat. No. 11252.

3. Isocitrate dehydrogenase, from Sigma, Cat. No. 12002.

Preparation of liver microsome solution (final concentration: 0.5 mg protein/mL)

| Microsome | product information | Source |
|---|---|---|
| Human liver microsome | Cat No. 452117 Lot No. 38291 | BD Biosciences |
| Rat liver microsome | Cat No. R1000 Lot No. 1310030 | Xenotech |
| Canine liver microsome | Cat No. D1000 Lot No. 1310086 | Xenotech |

Stop Solution

Cold acetonitrile containing 100 ng/mL tolbutamide and 100 ng/mL labetalol was used as the internal standard.

Experimental Method

10 µL of the working solution of the test compound or reference compound was added to all plates ($T_0$, $T_5$, $T_{10}$, $T_{20}$, $T_{30}$, $T_{60}$, $NCF_{60}$).

680 µL of liver microsome solution was added to each well of 96-well plates, then 80 µL was added to each well of the plates, and the plates were placed at 37° C. for pre-incubation for approximately 10 minutes.

10 µL of 100 mM potassium phosphate buffer was added to each well of the $NCF_{60}$ plate.

After the pre-incubation, 90 µL NADPH regeneration system working solution was added to each well the 96-well plates, and then 10 µL was added to each well of the plates to initiate the reaction.

Incubation for an appropriate time (such as 5, 10, 20, 30, and 60 minutes).

300 µL of the stop solution (refrigerated at 4° C., containing 100 ng/mL tolbutamide and 100 ng/mL labetalol) was added into each sample well.

The sample plate was shaken for about 10 minutes and centrifuged at 4000 rpm for 20 minutes at 4° C.

During centrifugation, 300 µL of HPLC water was added to each well, and 100 µL of the supernatant was collected for LC-MS/MS analysis.

Data Analysis

The half-life T/2 and the intrinsic clearance by liver microsome $C_{lint(mic)}$ were calculated by the following formulas:

$$C_t = C_0 \bullet e^{-k_e \bullet t}$$

When $C_t = \frac{1}{2}C_0$, $$T_{1/2} = \frac{Ln2}{k_e} = \frac{0.693}{k_e}$$

$$CL_{int(mic)} = \frac{0.693}{T_{1/2}} \bullet \frac{1}{\text{Microsomal protein concentration during incubation (mg/mL)}}$$

$$CL_{int(liver)} = CL_{int(mic)} \bullet \frac{\text{Microsomal protein (mg)}}{\text{Liver weight (g)}} \bullet \frac{\text{Liver weight (g)}}{\text{Body weight (kg)}}$$

$$C_t = C_0 \bullet e^{-k_e \bullet t}$$

When $C_t = \frac{1}{2}C_0$, $$T_{1/2} = \frac{Ln2}{k_e} = \frac{0.693}{k_e}$$

$$CL_{int(mic)} = \frac{0.693}{T_{1/2}} \bullet \frac{1}{\text{Microsomal protein concentration during incubation (mg/mL)}}$$

$$CL_{int(liver)} = CL_{int(mic)} \bullet \frac{\text{Microsomal protein (mg)}}{\text{Liver weight (g)}} \bullet \frac{\text{Liver weight (g)}}{\text{Body weight (kg)}}$$

Each gram of liver contained 45 mg of microsomal protein, and the liver weights of mice, rats, dogs, monkeys and humans were 88 g/kg, 40 g/kg, 32 g/kg, 30 g/kg and 20 g/kg, respectively.

$C_t$ is the concentration at time t, t is the incubation time, $C_0$ is the concentration at 0, $k_e$ is the elimination rate constant, $Cl_{int(mic)}$ is the intrinsic clearance rate by liver microsome, and $Cl_{int(liver)}$ is the intrinsic clearance rate by liver.

Experimental Results

The results are shown in Table 4.

TABLE 4

Clearance rate of compounds D1, 2, 3 and 7 by human and rat liver microsome

| Number of the compound | Intrinsic clearance by liver microsome (mL/min/Kg) | |
|---|---|---|
|  | Human | Rat |
| Reference compound D1 | 52.1 | 52.9 |
| Compound 2 | 54.6 | 25.5 |
| Compound 3 | 45.3 | <17.3 |
| Compound 7 | 51.7 | 24.9 |

The results show that the compounds of the present disclosure have comparable or better liver microsomal metabolic stability than the reference compound D1 in human and rat species.

Study on In Vivo Pharmacokinetics in Rats after Single Administration

Experimental Objective

Male SD rats were used as test animals, and the concentration of the compound in blood was determined after single administration to evaluate the pharmacokinetic behavior.

Experimental Materials:

Sprague Dawley rats (male, 200-300 g, 7-9 weeks, Shanghai Charles River Laboratory Animal Co., Ltd.)

Experimental Operation:

The pharmacokinetic characteristics of the test compound in rodents after intravenous injection and oral administration were tested by standard protocols, in the experiment, the test compound was prepared into a clear solution or homogeneous suspension, and administered to the rats by single intravenous injection and oral administration. In the intravenous injection group, the menstruum was a certain proportion of ethanol and physiological saline solution or a certain proportion of dimethyl sulfoxide in HP-β cyclodextrin solution (pH was adjusted to 3-4), the mixture was vortexed and stirred to prepare 2 mg/mL or 1 mg/mL clear solution, then filtered with microporous membrane for later use; in the oral administration group, the menstruum was a certain proportion of sodium carboxymethyl cellulose solution or a certain proportion of dimethyl sulfoxide in HP-0 cyclodextrin solution (pH was adjusted to about 4), after the test compound was mixed with the solvent, the mixture was vortexed and stirred to prepare 2 mg/mL or 1 mg/mL homogeneous suspension or clear solution for later use. After 2 mg/kg intravenous administration or 10 mg/kg oral administration to rats, a certain amount of whole blood samples were collected, centrifuged at 3000 g for 15 minutes, the supernatant was separated to give the plasma samples; then an acetonitrile solution containing internal standard with a volume 3 times that of the plasma sample was added to precipitate proteins, and then centrifuged; the supernatant was separated, and water with a volume twice that of the supernatant was added to the supernatant, which was then centrifuged again; the supernatant was collected for analysis; LC-MS/MS analysis method was used to quantitatively analyze the blood drug concentration, and Phoenix WinNonlin software (Pharsight, USA) was used to calculate the pharmacokinetic parameters, such as peak concentration, time to peak concentration, clearance rate, half-life, area under the concentration-time curve, bioavailability, etc.

Experimental Results:

TABLE 5

Pharmacokinetic properties of compound 7 in rats

| Number of the compound | | Compound 7 |
|---|---|---|
| 2 mpk intravenous injection | $C_0$ (nM) | 5385 |
| | $T_{1/2}$ (hr) | 0.55 |
| | $Vd_{ss}$ (L/kg) | 0.81 |
| | Cl (mL/min/kg) | 22.4 |
| | $AUC_{0\text{-}inf}$ (nM · hr) | 2611 |
| 10 mpk oral administration | $C_{max}$ (nM) | 1792 |
| | $T_{max}$ (hr) | 0.63 |
| | $T_{1/2}$ (hr) | 1.60 |
| | $AUC_{0\text{-}inf}$ (nM · hr) | 3236 |
| | Bioavailability | 24.8% |

Among them, $C_0$ is the initial concentration, $T_{1/2}$ is the elimination half-life, $V_{dss}$ is the steady-state apparent volume of distribution, Cl is the total clearance rate, $AUC_{0\text{-}inf}$ is the area under the plasma drug concentration-time curve from time 0 to infinity, $C_{max}$ is the peak concentration, $T_{max}$ is the time to peak concentration.

The results show that: the compounds of the present disclosure have good pharmacokinetic properties and oral bioavailability in rats.

Study on In Vivo Pharmacokinetics in Mice after Single Administration

Experimental Objective

Male CD-1 mice were used as test animals, the concentration of the compound in blood was determined after single administration to evaluate the pharmacokinetic behavior.

Experimental Materials:

CD-1 mice (male, 20-40 g, 6-9 weeks, Shanghai Sippr-Bk Laboratory Animal Co., Ltd.)

Experimental Operation:

The pharmacokinetic characteristics of the test compound in rodents after intravenous injection and oral administration were tested by standard protocols, in the experiment, the test compound was prepared into a clear solution or homogeneous suspension, and administered to the mice by single intravenous injection and oral administration. In the intravenous injection group, the menstruum was a certain proportion of ethanol, Cremophor EL and physiological saline solution, the mixture was vortexed to prepare 1 mg/mL clear solution, then filtered with microporous membrane for later use; in the oral administration group, the menstruum was a certain proportion of methyl cellulose solution or certain proportion of methyl cellulose and Tween 80 aqueous solution, the test compound was mixed with the menstruum, and the mixture was vortexed to prepare 10 mg/mL clear or homogeneous suspension for later use. After 2 mg/kg intravenous administration or 100 mg/kg oral administration to the mice, a certain amount of whole blood samples were collected, centrifuged at 3200 g for 10 minutes, the supernatant was separated to give the plasma samples, and the samples were diluted multiple times with blank plasma according to actual needs. The plasma sample was added to acetonitrile solution containing the internal standard with a volume 20 times that of the plasma sample to precipitate proteins, and then centrifuged; the supernatant was separated, and water with a volume twice that of the supernatant was added to the supernatant, which was then centrifuged again; the supernatant was collected for analysis; LC-MS/MS analysis method was used to quantitatively analyze the blood drug concentration, and Phoenix WinNonlin software (Pharsight, USA) was used to calculate the pharmacokinetic parameters, such as peak concentration, time to peak concentration, clearance rate, half-life, area under the concentration-time curve, bioavailability, etc.

Experimental Results:

TABLE 6

Pharmacokinetic properties of compound 7 in mice

| Number of the compound | | Compound 7 |
|---|---|---|
| 2 mpk intravenous injection | $C_0$ (nM) | 2720 |
| | $T_{1/2}$ (hr) | 0.57 |
| | $Vd_{ss}$ (L/kg) | 1.54 |
| | Cl (mL/min/kg) | 41.7 |
| | $AUC_{0-inf}$ (nM · hr) | 1438 |
| 100 mpk oral administration | $C_{max}$ (nM) | 25550 |
| | $T_{max}$ (hr) | 0.38 |
| | $T_{1/2}$ (hr) | 0.92 |
| | $AUC_{0-inf}$ (nM · hr) | 37567 |
| | Bioavailability | 52.2% |

Among them, $C_0$ is the initial concentration, $T_{1/2}$ is the elimination half-life, $V_{dss}$ is the steady-state apparent volume of distribution, Cl is the total clearance rate, $AUC_{0-inf}$ is the area under the plasma drug concentration-time curve from time 0 to infinity, $C_{max}$ is the peak concentration, $T_{max}$ is the time to peak concentration.

The results show that: the compound 7 of the present disclosure has good pharmacokinetic properties and oral bioavailability in mice.

Study on in vivo pharmacokinetics in beagle dogs after single administration

Experimental Objective

Male beagle dogs were used as test animals, the concentration of the compound in blood after single administration was determined to evaluate the pharmacokinetic behavior.

Experimental Materials:

Beagle dogs (Male, 6-12 kg, more than 6 months, Beijing Marshall Biotechnology Co., Ltd.).

Experimental Operation:

The objective of the test was to study the pharmacokinetic characteristics of the test compound in non-rodent after intravenous injection and oral administration. In the experiment, the test compound was prepared into a clear solution or homogeneous suspension and administered to the beagle dogs by single intravenous injection or oral administration. In the intravenous injection group, the menstruum was a certain proportion of dimethyl sulfoxide in HP-β-cyclodextrin solution or a certain proportion of ethanol, polyethylene glycol 400 and physiological saline solution, the mixture was vortexed and subjected to ultrasonic treatment to prepare 2 mg/mL or 1 mg/kg clear solution, then filtered with microporous membrane for later use; in the oral administration group, the menstruum was a certain proportion of dimethyl sulfoxide in HP-β-cyclodextrin solution or a certain proportion of sodium carboxymethyl cellulose solution, the test compound was mixed with the menstruum, vortexed and subjected to ultrasonic treatment to prepare 2 mg/mL clear solution or 1 mg/mL homogeneous suspension for later use. After 2 mg/kg or 1 mg/kg intravenous administration or 10 mg/kg or 5 mg/kg oral administration to the Beagle dogs, a certain amount of whole blood samples were collected, centrifuged at 3000 g for 10 minutes, and the supernatant was separated to obtain plasma samples; then an acetonitrile solution containing internal standard with a volume 10 times that of the plasma sample was added to precipitate proteins, and then centrifuged; the supernatant was separated for analysis; LC-MS/MS analysis method was used to quantitatively analyze the blood drug concentration, and Phoenix WinNonlin software (Pharsight, USA) was used to calculate the pharmacokinetic parameters, such as peak concentration, time to peak concentration, clearance rate, half-life, area under the concentration-time curve, bioavailability, etc.

Experimental Results

TABLE 7

Pharmacokinetic properties of compound 7 in dogs

| Number of the compound | | Compound 7 |
|---|---|---|
| 2 mpk intravenous injection | $C_0$ (nM) | 8463 |
| | $T_{1/2}$ (hr) | 0.44 |
| | $Vd_{ss}$ (L/kg) | 0.49 |
| | Cl (mL/min/kg) | 12.4 |
| | $AUC_{0-inf}$ (nM · hr) | 4664 |
| 10 mpk oral administration | $C_{max}$ (nM) | 3945 |
| | $T_{max}$ (hr) | 0.63 |
| | $T_{1/2}$ (hr) | 2.20 |
| | $AUC_{0-inf}$ (nM · hr) | 7690 |
| | Bioavailability | 33.0% |

Among them, $C_0$ is the initial concentration, $T_{1/2}$ is the elimination half-life, $V_{dss}$ is the steady-state apparent volume of distribution, Cl is the total clearance rate, $AUC_{0-inf}$ is the area under the plasma drug concentration-time curve from time 0 to infinity, $C_{max}$ is the peak concentration, $T_{max}$ is the time to peak concentration.

The results show that: the compound 7 of the present disclosure has good pharmacokinetic properties and oral bioavailability in beagle dogs.

What is claimed is:

1. A compound represented by formula (I) and formula (II), a stereoisomer thereof or a pharmaceutically acceptable salt thereof,

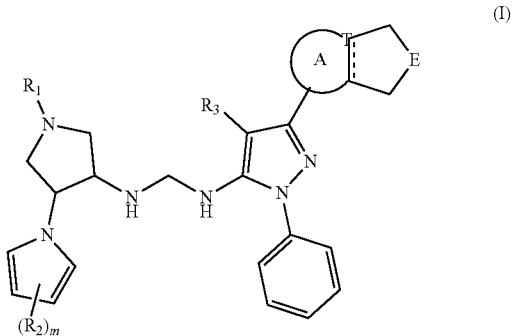

(I)

-continued

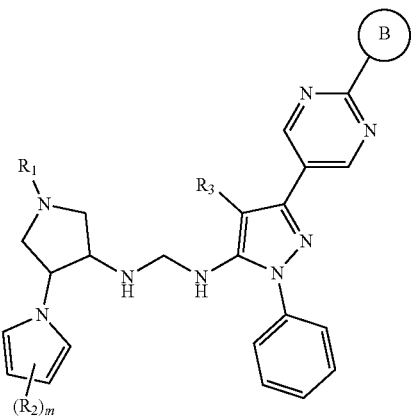

(II)

wherein,

⫽ is selected from a single bond and a double bond;
T is selected from N and C;
E is selected from O, NR$_4$ and CR$_5$R$_6$;
R$_1$ is selected from C$_{1-6}$ alkyl optionally substituted by 1, 2 or 3 R$_a$;
each of R$_2$ is independently selected from H, F, Cl, Br, I, OH and NH$_2$;
R$_3$ is selected from C$_{1-3}$ alkyl optionally substituted by 1, 2 or 3 R$_b$;
R$_4$ is selected from H, and C$_{1-6}$ alkyl optionally substituted by 1, 2 or 3 R$_c$;
each of R$_5$ and R$_6$ is independently selected from H, F, Cl, Br, I, OH, NH$_2$, CN, COOH, and C$_{1-3}$ alkyl optionally substituted by 1, 2 or 3 R$_d$;
ring A is selected from 5-6 membered heteroaryl;
ring B is selected from 4-6 membered heterocycloalkyl optionally substituted by 1, 2 or 3 R$_e$;
m is selected from 1, 2 and 3;
each of R$_a$, R$_b$, R$_c$, R$_d$ and R$_e$ is independently selected from F, Cl, Br, I, OH, NH$_2$, CN, COOH, C$_{1-3}$ alkyl and C$_{1-3}$ alkoxy, wherein the C$_{1-3}$ alkyl and C$_{1-3}$ alkoxy are optionally substituted by 1, 2 or 3 R;
R is selected from F, Cl, Br, I, OH and NH$_2$;
each of the 4-6 membered heterocycloalkyl and the 5-6 membered heteroaryl contains 1, 2, 3 or 4 heteroatoms or heteroatom groups independently selected from —NH—, —O—, —S— and N.

2. The compound, the stereoisomer thereof or the pharmaceutically acceptable salt thereof as defined in claim 1, wherein, each of R$_a$, R$_b$, R$_c$, R$_d$ and R$_e$ is independently selected from F, Cl, Br, I, OH, NH$_2$, CN, COOH, CH$_3$ and OCH$_3$.

3. The compound, the stereoisomer thereof or the pharmaceutically acceptable salt thereof as defined in claim 1, wherein, R$_1$ is selected from C$_{1-3}$ alkyl optionally substituted by 1, 2 or 3 R$_a$.

4. The compound, the stereoisomer thereof or the pharmaceutically acceptable salt thereof as defined in claim 3, wherein, R$_1$ is selected from

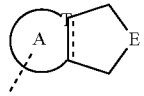

5. The compound, the stereoisomer thereof or the pharmaceutically acceptable salt thereof as defined in claim 1, wherein, R$_3$ is selected from CH$_3$ and CH$_2$CH$_3$.

6. The compound, the stereoisomer thereof or the pharmaceutically acceptable salt thereof as defined in claim 1, wherein, R$_4$ is selected from H and C$_{1-3}$ alkyl optionally substituted by 1, 2 or 3 R$_c$.

7. The compound, the stereoisomer thereof or the pharmaceutically acceptable salt thereof as defined in claim 6, wherein, R$_4$ is selected from H, CH$_3$, CH$_2$CH$_3$ and CH$_2$CH$_2$OH.

8. The compound, the stereoisomer thereof or the pharmaceutically acceptable salt thereof as defined in claim 1, wherein, each of R$_5$ and R$_6$ is independently selected from H, F, Cl, Br, I, OH, NH$_2$, CN, COOH and CH$_3$.

9. The compound, the stereoisomer thereof or the pharmaceutically acceptable salt thereof as defined in claim 1, wherein, ring A is selected from pyridyl and pyrazolyl.

10. The compound, the stereoisomer thereof or the pharmaceutically acceptable salt thereof as defined in claim 1, wherein, the structural unit

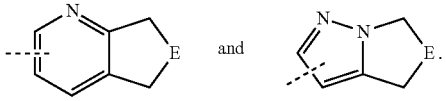

is selected from

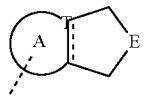

11. The compound, the stereoisomer thereof or the pharmaceutically acceptable salt thereof as defined in claim 10, wherein, the structural unit

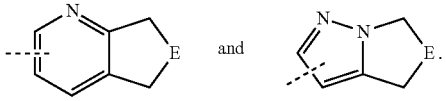

is selected from

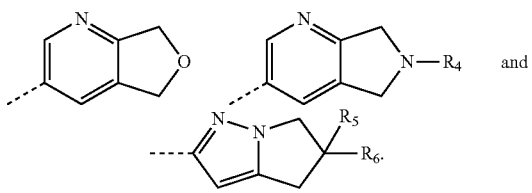

12. The compound, the stereoisomer thereof or the pharmaceutically acceptable salt thereof as defined in claim 11, wherein, the structural unit

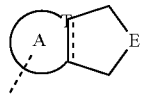

is selected from

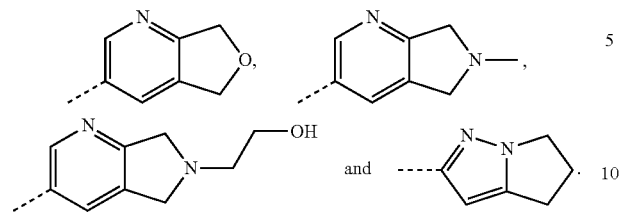

13. The compound, the stereoisomer thereof or the pharmaceutically acceptable salt thereof as defined in claim 1, wherein, ring B is selected from oxetanyl and azetidinyl, wherein the oxetanyl and the azetidinyl are optionally substituted by 1, 2 or 3 $R_c$.

14. The compound, the stereoisomer thereof or the pharmaceutically acceptable salt thereof as defined in claim 13, wherein, ring B is selected from

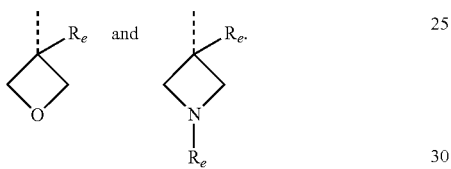

15. The compound, the stereoisomer thereof or the pharmaceutically acceptable salt thereof as defined in claim 14, wherein, ring B is selected from

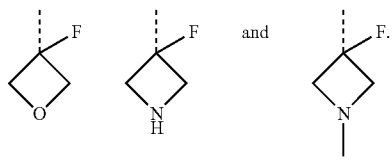

16. The compound, the stereoisomer thereof or the pharmaceutically acceptable salt thereof as defined in claim 1, which is selected from:

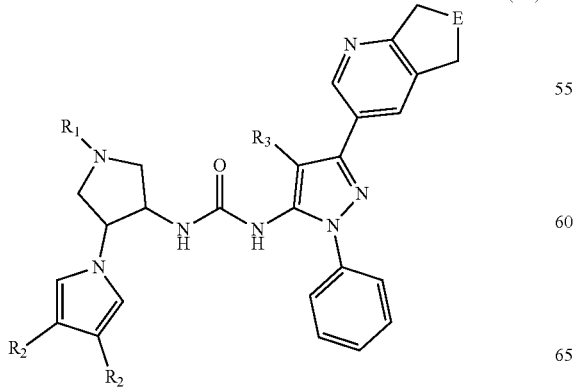

(I-1)

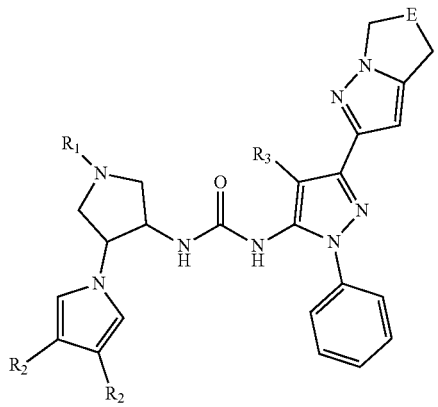

(I-2)

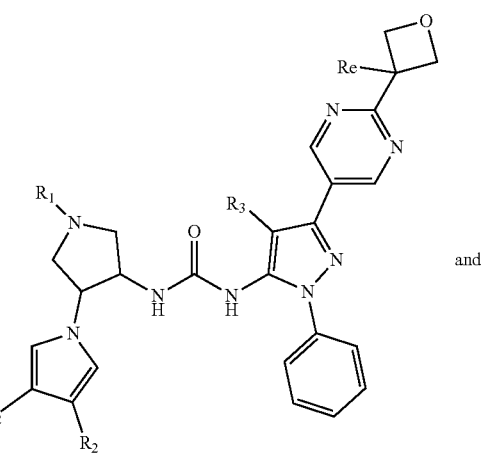

(I-3) and

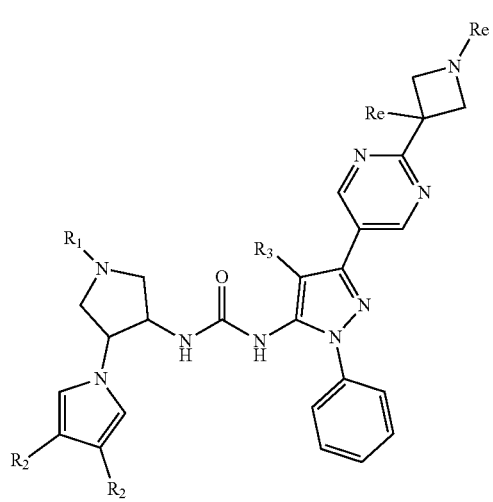

(I-4)

17. The compound, the stereoisomer thereof or the pharmaceutically acceptable salt thereof as defined in claim 16, which is selected from:
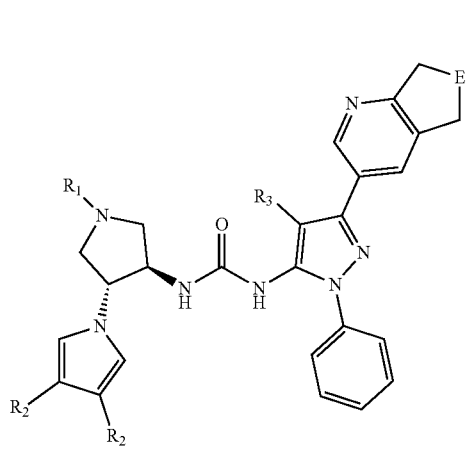
(I-1a)
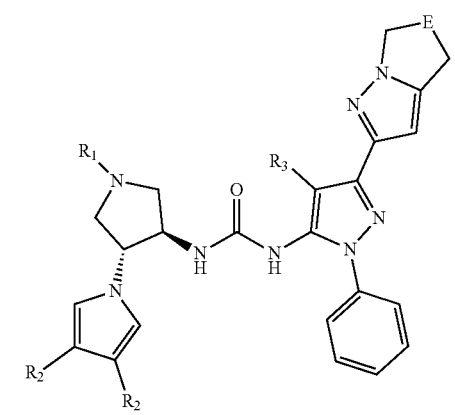
(I-2a)
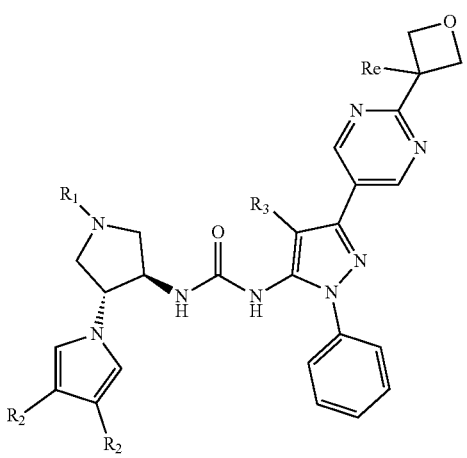
(I-3a)
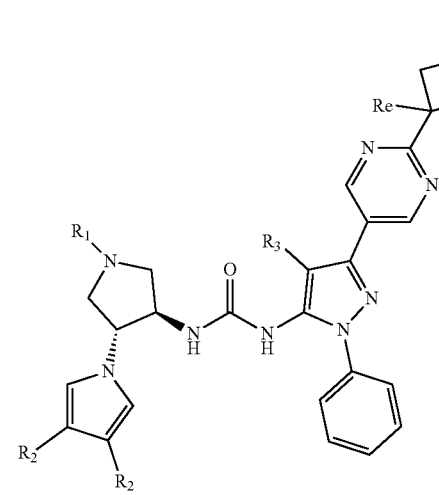
(I-4a)
18. A compound, a stereoisomer thereof or a pharmaceutically acceptable salt thereof, wherein the compound is selected from:
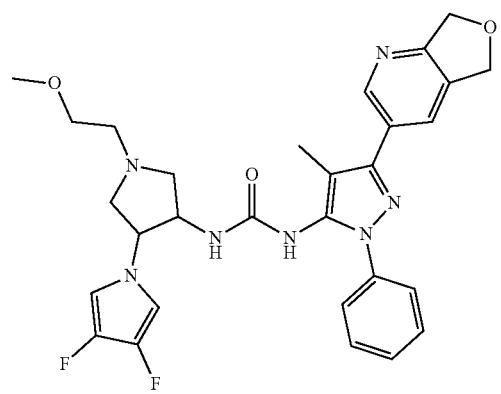
and
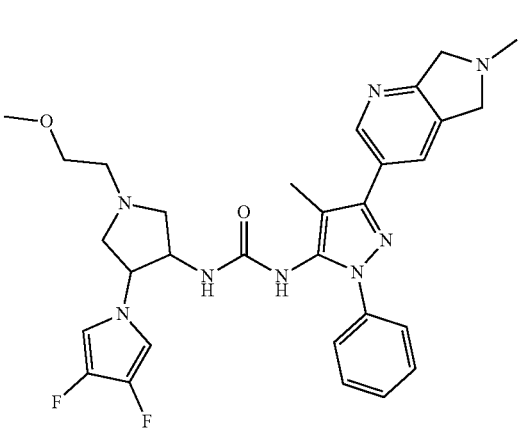

65
-continued
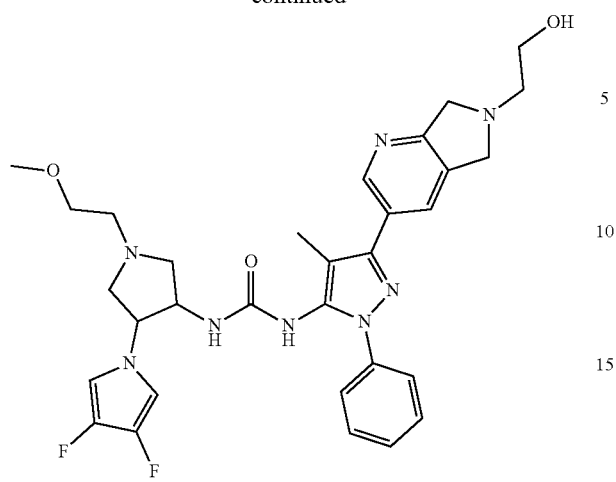
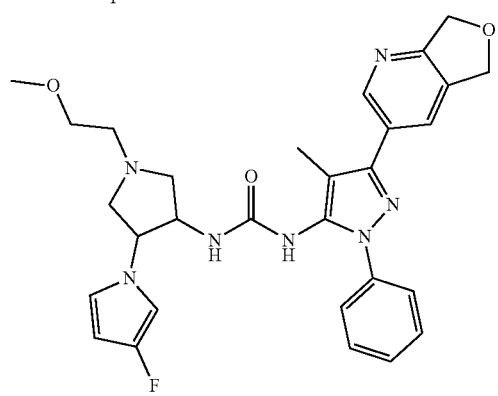
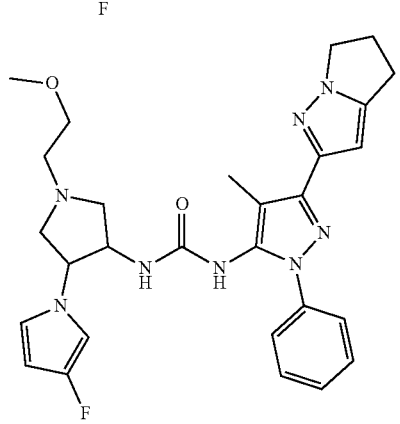
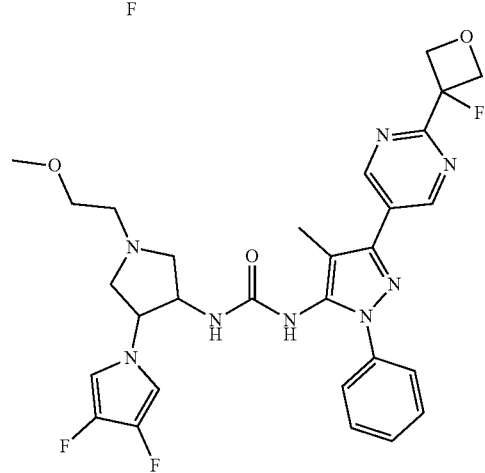
66
-continued
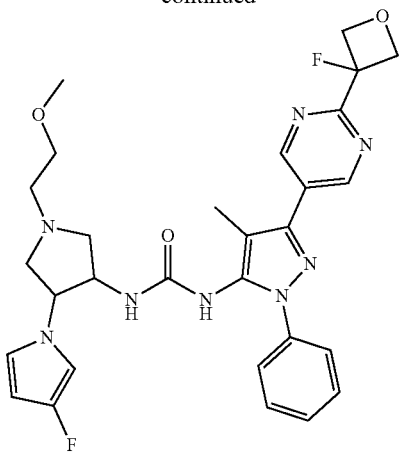
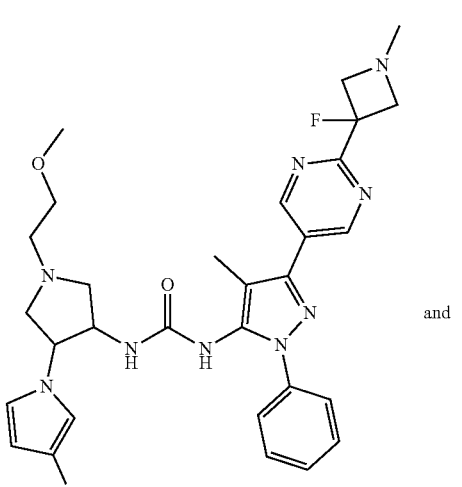
and
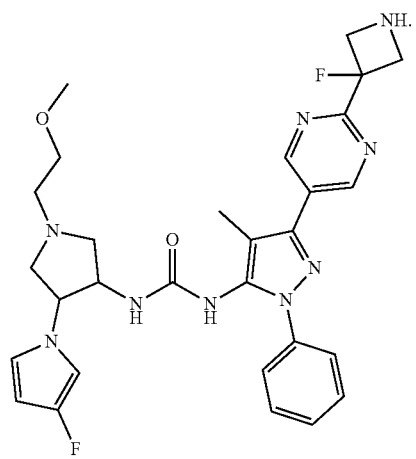

19. The compound, the stereoisomer thereof or the pharmaceutically acceptable salt thereof as defined in claim 18, which is selected from:
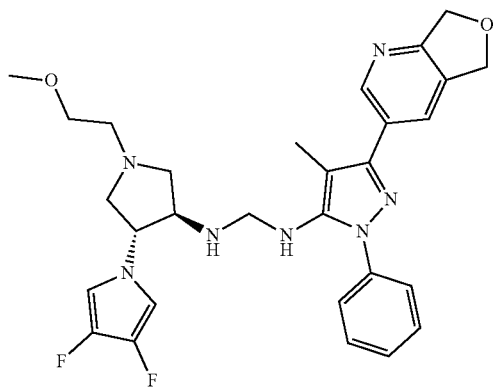
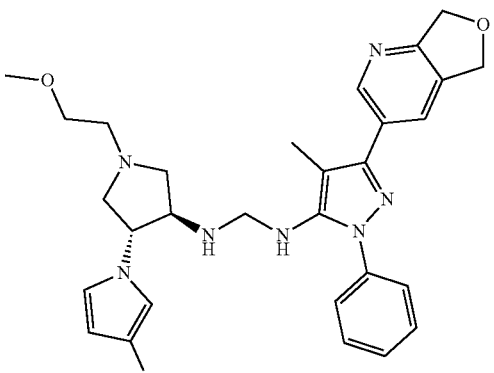
-continued
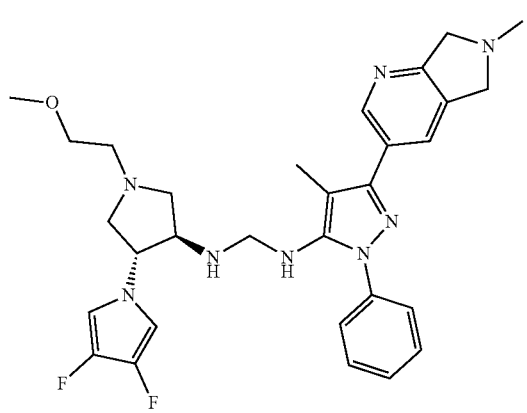
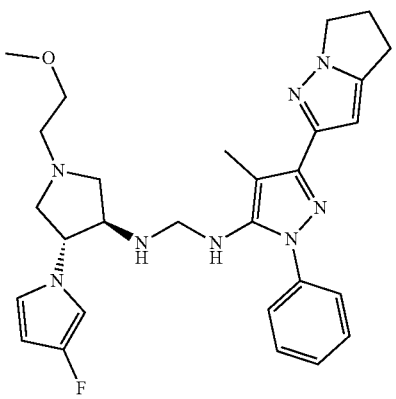
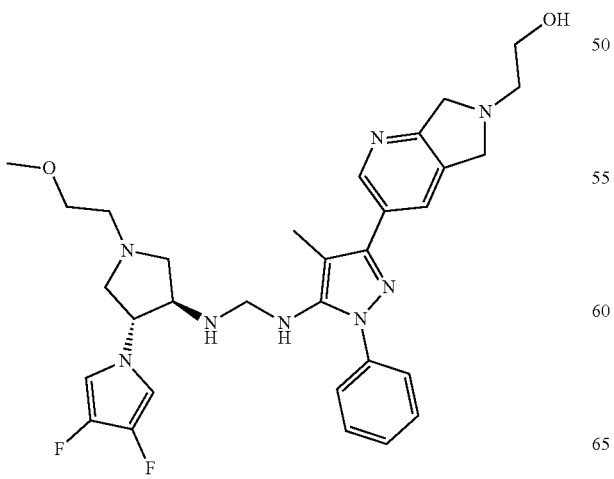
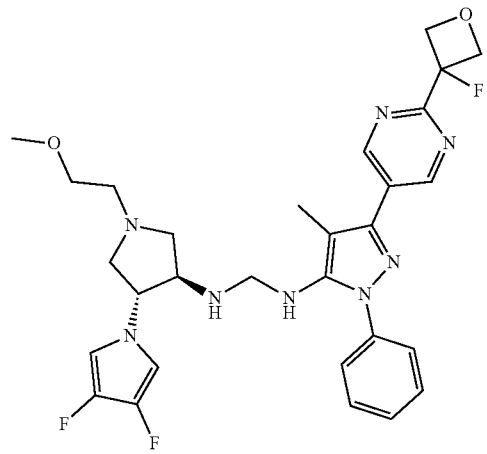

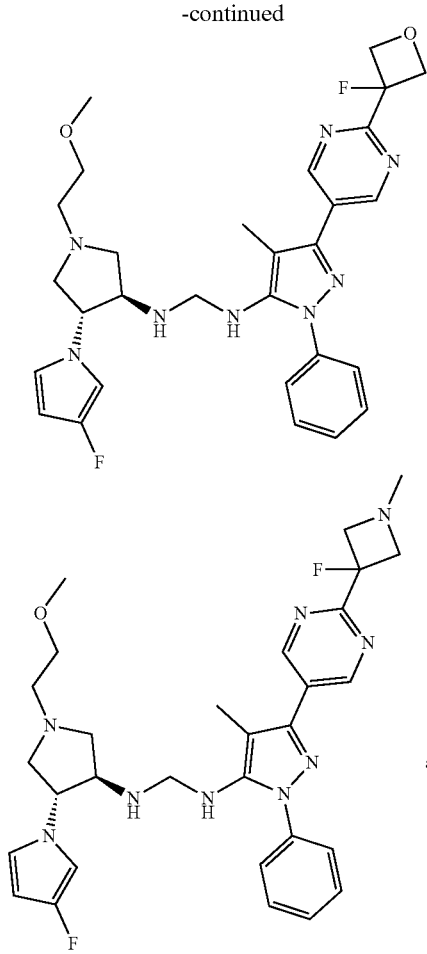
and
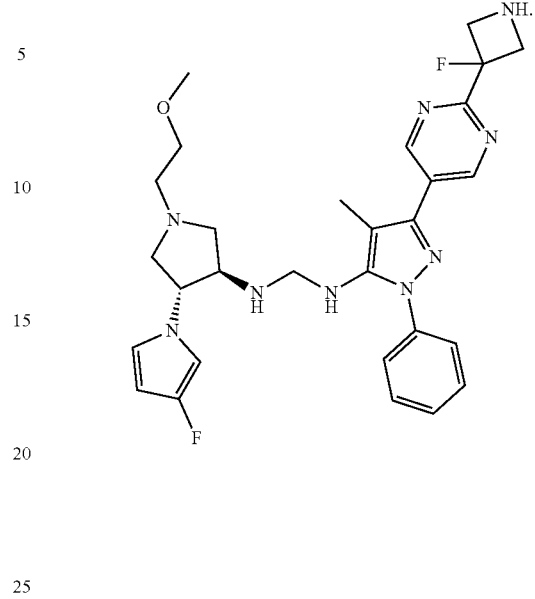
20. A method for treating diseases related to TrKA in a subject in need thereof, comprising administering an effective amount of the compound, the stereoisomer or the pharmaceutically acceptable salt thereof as defined in claim 1 to the subject.
* * * * *